United States Patent

Sakamoto et al.

Patent Number: 5,151,428
Date of Patent: Sep. 29, 1992

[54] PYRIDINE DERIVATIVES AND THEIR COMPOSITIONS FOR THE CONTROL OF INSECT PESTS

[76] Inventors: Noriyasu Sakamoto, 4-1-404, Ryodo-cho, Nishinomiya, Hyogo; Hirosi Kisida, 2-1-12-402, Nigawatakamaru, Takarazuka, Hyogo; Hiroaki Fujimoto, 2-11-7-407, Sonehigashiono-cho, Toyonaka, Osaka; Kimitoshi Umeda, 2-11-8-307, Sonehigashino-cho, Toyonaka, Osaka; Noritada Matsuo, 29-2, Minaminoazayamamichi, Itami, Hyogo, all of Japan

[21] Appl. No.: 705,383

[22] Filed: May 24, 1991

[30] Foreign Application Priority Data

May 24, 1990 [JP] Japan .................................. 2-136497

[51] Int. Cl.$^5$ ..................... A01N 43/40; C07D 213/02
[52] U.S. Cl. .................... 514/277; 514/345; 514/348; 514/351; 514/357; 546/1; 546/290; 546/296; 546/300; 546/301; 546/302; 546/303; 546/329; 546/334; 546/338; 546/339; 546/340; 546/345; 546/346
[58] Field of Search ............. 546/339, 340, 1, 338, 546/290, 296, 300, 301, 302, 303, 329, 334, 346, 345; 514/277, 345, 348, 351, 357

[56] References Cited

U.S. PATENT DOCUMENTS

| | | | |
|---|---|---|---|
| 4,036,844 | 7/1977 | Thorne et al. | 546/339 |
| 4,053,607 | 10/1977 | Thorne et al. | 514/348 |
| 4,943,585 | 7/1990 | Buerstinghaus et la. | 514/398 |

FOREIGN PATENT DOCUMENTS

| | | |
|---|---|---|
| 0101288 | 2/1984 | European Pat. Off. |
| 0289919 | 9/1988 | European Pat. Off. |
| 0299694 | 1/1989 | European Pat. Off. |
| 2516331 | 11/1975 | Japan |

*Primary Examiner*—C. Warren Ivy
*Assistant Examiner*—James H. Turnipseed

[57] ABSTRACT

A pyridine derivative of the formula:

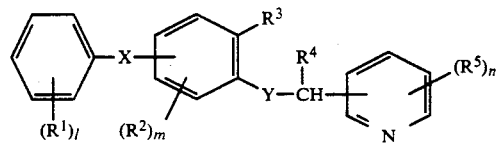

wherein $R^1$ is, the same or different, each a hydrogen atom, a halogen atom, a $C_1$–$C_4$ alkyl group, a $C_1$–$C_4$ haloalkyl group, a $C_1$–$C_3$ alkoxy gorup, a $C_1$–$C_3$ haloalkoxy group, a cyano group or a nitro group; $R^2$ is, the same or different, each a hydrogen atom, a halogen atom or a methyl group; $R^3$ is a halogen atom or a $C_1$–$C_3$ alkyl group; $R_4$ is a hydrogen atom or a $C_1$–$C_3$ alkyl group; $R^5$ is, the same or different, each a halogen atom, a $C_1$–$C_3$ alkyl group, a $C_1$–$C_3$ haloalkyl group, a $C_1$–$C_3$ alkoxy group or a $C_1$–$C_3$ haloalkoxy group; X is an oxygen atom, a sulfur atom, a carbonyl group, a sulfinyl group, a sulfonyl group, an imino group or a methylene group; Y is an oxygen atom or a sulfur atom; l is an integer of 1 to 5; m is an integer of 1 to 3; and n is an integer of 1 to 4, which is useful for control of insect pest.

24 Claims, No Drawings

PYRIDINE DERIVATIVES AND THEIR COMPOSITIONS FOR THE CONTROL OF INSECT PESTS

BACKGROUND OF THE INVENTION

1. Field of the Invention

The present invention relates to pyridine derivatives, their production processes and their compositions for the control of insect pests.

2. Description of the Prior Art

It is described in German Offenlegungsschrift 2,516,331 that certain pyridine derivatives are useful as insecticides and acaricides. But, their insecticidal and acaricidal activities are still not satisfactory.

SUMMARY OF THE INVENTION

As a result of the extensive study seeking pyridine compounds producing a satisfactory controlling effect on insect pests, it has been found that pyridine derivatives of the following formula exhibit a remarkable juvenile hormone-like activity and can control significantly the growth of insect pests:

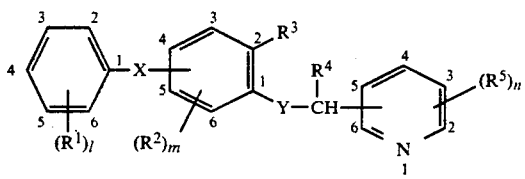

wherein $R^1$ is, the same or different, each a hydrogen atom, a halogen atom, a $C_1$–$C_4$ alkyl group, a $C_1$–$C_4$ haloalkyl group, a $C_1$–$C_3$ alkoxy group, a $C_1$–$C_3$ haloalkoxy group, a cyano group or a nitro group; $R^2$ is, the same or different, each a hydrogen atom, a halogen atom or a methyl group; $R^3$ is a halogen atom or a $C_1$–$C_3$ alkyl group; $R_4$ is a hydrogen atom or a $C_1$–$C_3$ alkyl group; $R^5$ is, the same or different each a halogen atom, a $C_1$–$C_3$ alkyl group, a $C_1$–$C_3$ haloalkyl group, a $C_1$–$C_3$ alkoxy group or a $C_1$–$C_3$ haloalkoxy group; X is an oxygen atom (—O—), a sulfur atom (—S—), a carbonyl group (—CO—), a sulfinyl group (—SO—), a sulfonyl group (—SO$_2$—), an imino group (—NH—) or a methylene group (—CH$_2$—); Y is an oxygen atom (—O—) or a sulfur atom (—S—); l is an integer of 1 to 5; m is an integer of 1 to 3; and n is an integer of 1 to 4.

The present invention is based on the above finding.

DETAILED DESCRIPTION OF THE INVENTION

The pyridine derivatives (I) of the invention have an excellent juvenile hormone-like activity against insect pests. They exhibit various actions such as metamorphosis inhibition, embryogenesis inhibition and sterilization and are thus efficacious as growth regulators, chemosterilants, ovicides or reproduction inhibitory agents on various insect pests such as agricultural, forestal, hygienic and stored grain insect pests. They are also efficacious against insect pests having an increased resistance to commercial insecticides.

In the formula (I) which represents the pyridine derivatives of the invention, examples of the halogen atom are fluorine, chlorine, bromine, iodine, etc.

Examples of the $C_1$–$C_3$ alkyl group are methyl, ethyl, n-propyl, isopropyl, etc., while examples of the $C_1$–$C_4$ alkyl group are methyl, ethyl, n-propyl, isopropyl, n-butyl, sec-butyl, isobutyl, tert-butyl, etc. Examples of the $C_1$–$C_3$ haloalkyl group include trifluoromethyl, difluoromethyl, 2-fluoroethyl, 1-fluoroethyl, 1,2-difluor 2,2,2-trifluoroethyl, 2-chloroethyl, 3-fluoro-n-propyl, 2-fluoro-n-propyl, 1-fluoro-n-propyl, 3-chloro-n-propyl, 3-bromo-n-propyl, etc., while examples of the $C_1$–$C_4$ haloalkyl group include trifluoromethyl, difluoromethyl, 2-fluoroethyl, 1-fluoroethyl, 1,2-difluoroethyl, 2,2,2-trifluoroethyl, 2-chloroethyl, 3-fluoro-n-propyl, 2-fluoro-n-propyl, 1-fluoro-n-propyl, 3-chloro-n-propyl, 3-bromo-n-propyl, 4-fluoro-n-butyl, 4-chloro-n-butyl, etc. Examples of the $C_1$–$C_3$ alkoxy group include methoxy, ethoxy, n-propoxy, isopropoxy, etc. Examples of the $C_1$–$C_3$ haloalkoxy group include trifluoromethoxy, difluoromethoxy, bromodifluoromethoxy, 2-fluoroethoxy, 2,2,2-trifluoroethoxy, 1-fluoroethoxy, 1,2-difluoroethoxy, 3-fluoro-n-propoxy, 1-fluoro-n-propoxy, 2-fluoro-n-propoxy, 2-chloroethoxy, 3-chloro-n-propoxy, 3-bromo-n-propoxy, 1,1,2,2-tetrafluoroethoxy, 1,1-difluoromethoxy, etc.

Among the pyridine derivatives (I), preferred are those wherein $R^1$ is, the same or different, each a hydrogen atom, a fluorine atom, a chlorine atom, a bromine atom, a methyl group or a trifluoromethyl group. More preferred are those wherein $R^1$ is, the same or different, each a hydrogen atom, a fluorine atom or a chlorine atom, $R^2$ is a hydrogen atom or a chlorine atom, $R^3$ is a fluorine atom, a chlorine atom, a bromine atom or a methyl group, X is an oxygen atom or a methylene group, Y is an oxygen atom, l is an integer of 1 or 2, m is an integer of 1 and n is an integer of 1 or 2. Further more preferred are those wherein $(R^1)_l$ is 2,4-$F_2$, 3,5-$F_2$, 3,4-$Cl_2$, 3-F or 3-Cl, $R^2$ is a hydrogen atom, $R_3$ is a chlorine atom, $R^4$ is a hydrogen atom, $R^5$ is a chlorine atom or a methyl group, X is an oxygen atom or a methylene group, Y is an oxygen atom and m and n are each an integer of 1. When X is a methylene group, $R^1$ may be additionally a hydrogen atom. Most preferred are those wherein $(R^1)_l$ is 2,4-$F_2$, 3,5-$F_2$ or 3-Cl, $R^2$ is a hydrogen atom, $R^3$ is a chlorine atom, $R^4$ is a hydrogen atom, $R^5$ is a chlorine atom or a methyl group, X is an oxygen atom or a methylene group, Y is an oxygen atom and m and n are each an integer of 1. When X is a methylene group, $(R^1)_l$ may be additionally 3-F.

The optionally substituted phenyl-X- group may be present at any position from the 3- to 6-positions on the benzene ring but is preferred to exist at the 4- or 5-position. Also, the $R^4$-bearing methylene group may be attached to the substituted pyridyl group at any position of the latter but is preferred to attach at the 4- or 5-position, particularly at the 5-position. Further, the substituted pyridyl group may bear one or more substituents at any position, preferably at least at the 2-position.

The pyridine derivatives (I) of the invention can be produced by various processes, among which typical examples are shown below.

Process A

The pyridine derivative (I) is produced by reacting a phenol compound of the formula:

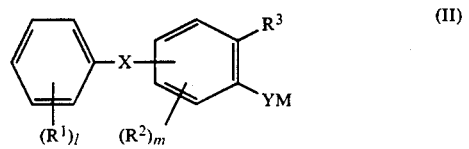

wherein M is an alkali metal atom or a hydrogen atom, $R^1$, $R^2$, $R^3$, X, Y, l and m are each as defined above with a halide of the formula:

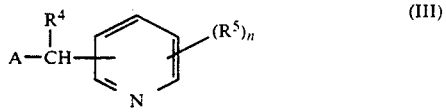

wherein A is a halogen atom and $R^4$, $R^5$ and n are each as defined above.

The reaction may be carried out usually in an inert solvent in the presence of a base at a temperature of from about $-20°$ C. to the boiling point of the inert solvent, preferably from about $-5°$ C. to the boiling point of the inert solvent. When the phenol compound (II) is employed in a metal salt form, the base is not necessarily required to use.

The molar proportion of the phenol compound (II) and the halide (III) to be used for the reaction is not limitative but is preferred to be nearly equal. Examples of the inert solvent are lower alcohols (e.g. methanol, ethanol, propanol, isopropanol, tert-butanol), ketones (e.g. acetone, methyl ethyl ketone), hydrocarbons (e.g. hexane, benzene, toluene), ethers (e.g. diethyl ether, diisopropyl ether, tetrahydrofuran, dioxane), acid amides (e.g. N,N-dimethylformamide, hexamethylphosphoric triamide), halogenated hydrocarbons (e.g. dichloromethane, chloroform, 1,2-dichloroethane, chlorobenzene), nitriles (e.g. acetonitrile), nitro compounds (e.g. nitromethane), dimethyl sulfoxide, water and mixtures thereof. Examples of the base are alkali metal hydroxides (e.g. sodium hydroxide, potassium hydroxide), alkali metal carbonates (e.g. potassium carbonate), alkali metals (e.g. metallic sodium), alkali metal hydrides (e.g. sodium hydride), organic bases (e.g. sodium methoxide, sodium ethoxide, triethylamine, pyridine), etc. When necessary or desired, an ammonium salt such as triethylbenzylammonium chloride may be added to the reaction system as a catalyst.

After completion of the reaction, post-treatment may follow in a per se conventional manner such as extraction with an organic solvent and concentration. When necessary or desired, the product may further be purified by chromatography, distillation, recrystallization, etc.

Process B

The pyridine derivative (I) is produced by reacting a phenol compound of the formula:

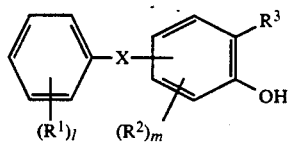

wherein $R^1$, $R^2$, $R^3$, X, l and m are each as defined above with an alcohol of the formula:

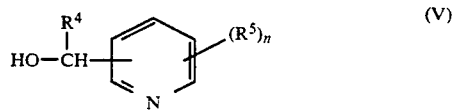

wherein $R^4$, $R^5$ and n are each as defined above. This process is advantageously applicable when $R^4$ is other than a hydrogen atom.

The reaction may be carried out normally in an inert solvent in the presence of a dehydrating catalyst or agent at a temperature of from about $-20°$ to 200 ° C. or the boiling point of the inert solvent.

The molar proportion of the phenol compound (IV) and the alcohol (V) is not limitative but is preferred to be nearly equal.

Examples of the dehydrating catalyst are inorganic acids (e.g. hydrochloric acid, sulfuric acid), aromatic sulfonic acids, sulfonic acid halides, etc. Examples of the dehydrating agent include dicyclohexylcarbodimide, di-isopropylazodicarboxylate, diethylazodicarboxylate, etc. Examples of the inert solvent are hydrocarbons (e.g. benzene, toluene, xylene), ethers (e.g. diethyl ether, diisopropyl ether, tetrahydrofuran, dioxane), halogenated hydrocarbons (e.g. carbon tetrachloride, dichloromethane, 1,2-dichloroethane, chlorobenzene, dichlorobenzene), etc.

After completion of the reaction, post-treatment may follow in a per se conventional manner such as extraction with an organic solvent and concentration. When necessary or desired, the product may further be purified by chromatography, distillation, recrystallization, etc.

The pyridine derivatives (I) of the invention have some asymemetric carbon atoms and can form optical isomers. Those optical isomers and their mixtures fall within the scope of the invention.

Among the starting compounds in the above processes, the phenol compound (II) wherein M is a hydrogen atom can be produced, for instance, as shown in the following scheme:

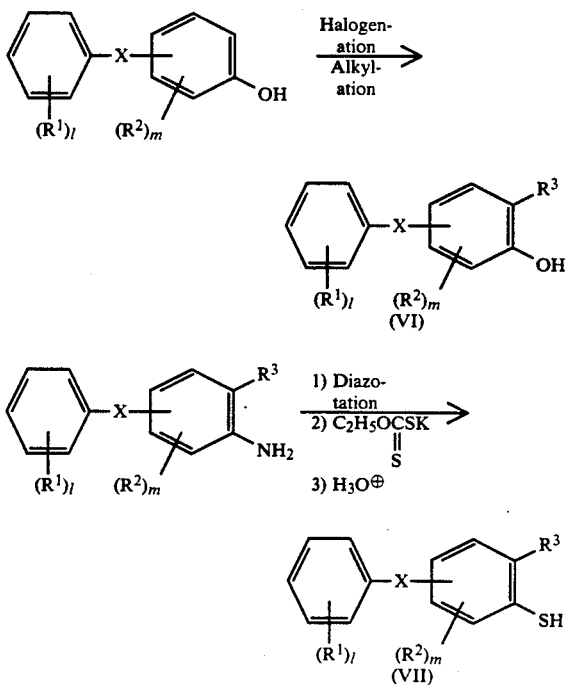

wherein $R^1$, $R^2$, $R^3$, X, l and m are each as defined above.

In the above scheme, each reaction may be performed by a per se conventional procedure. For instance, the phenol compound (VI) wherein $R^3$ is a chlorine atom may be prepared by reacting the corresponding non-chlorinated compound (i.e. the compound of the formula (VI) wherein $R^3$ is a hydrogen atom) with a chlorinating agent, preferably in an inert solvent. The molar proportion of the starting non-chlorinated compound and the chlorinating agent is not limitative, but it is ordinary to use the chlorinating agent in an amount equivalent to the non-chlorinating compound or somewhat in excess. Examples of the chlorinating agent are chlorine, tert-buthylhypochlorus acid, sulfuryl chloride, etc. If necessary and desired, the reaction can be carried out in the presence of a solvent. Examples of the inert solvent are dichloromethane, 1,2-dichloroethane, carbon tetrachloride, benzene, acetic acid, etc. The chlorinating agent itself may be available as a reaction medium when it is in liquid. The reaction temperature is usually from about $-80°$ C. to the refluxing temperature of the reaction system, preferably from about $-20°$ C. to the refluxing temperature of the reaction system.

After completion of the reaction, post-treatment may follow in a per se conventional manner such as extraction with an organic solvent and concentration. When necessary or desired, the product may further be purified by chromatography, distillation, recrystallization, etc.

Said starting non-chlorinated compound, i.e. the compound of the formula (VI) wherein $R^3$ is a hydrogen atom, can be produced according to the reaction scheme as shown in Reaction Scheme 2.

Reaction Scheme 2

X = O, S or NH:-

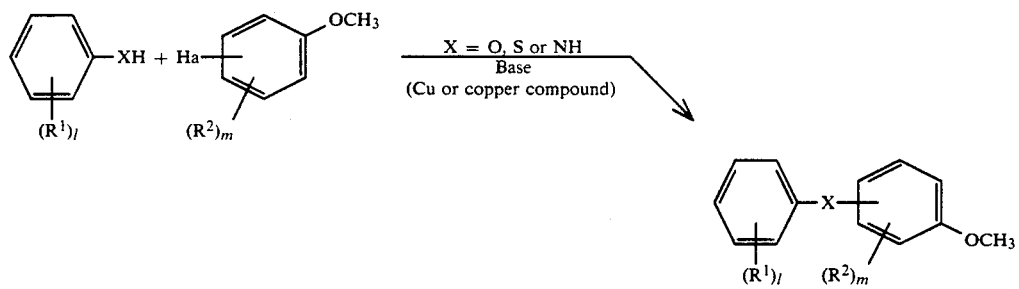

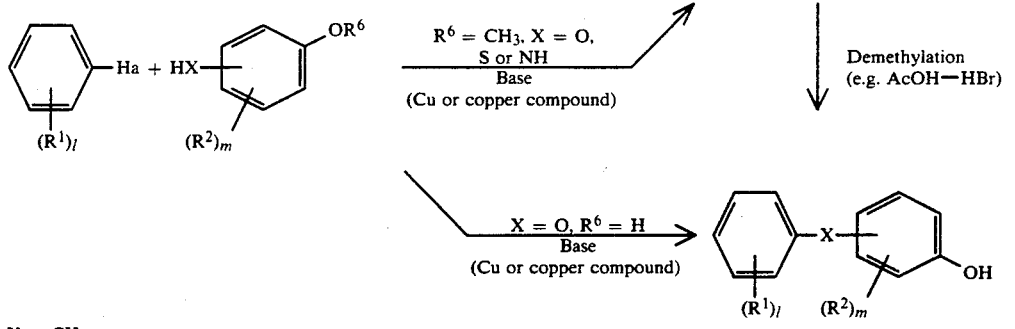

X = CH$_2$:-

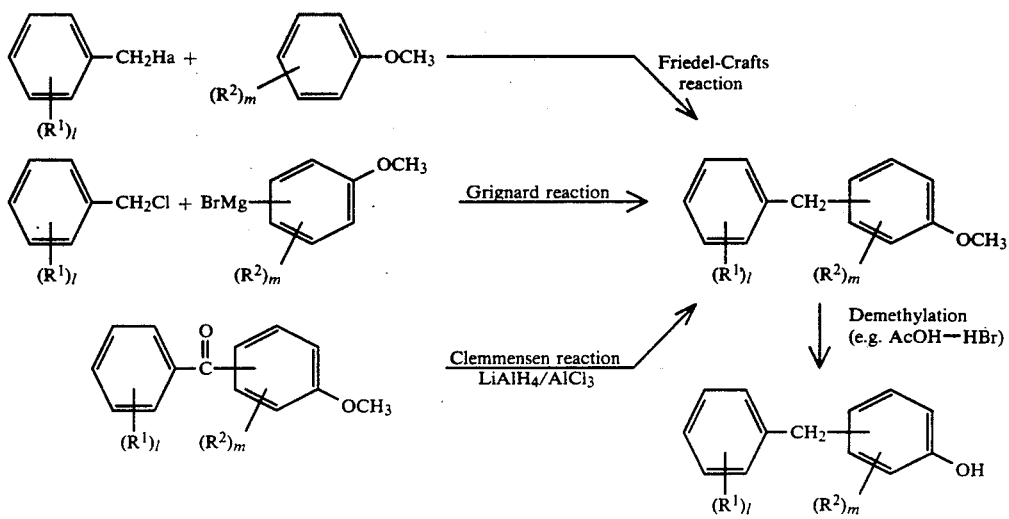

X = CO, SO or SO$_2$:-

-continued
Reaction Scheme 2

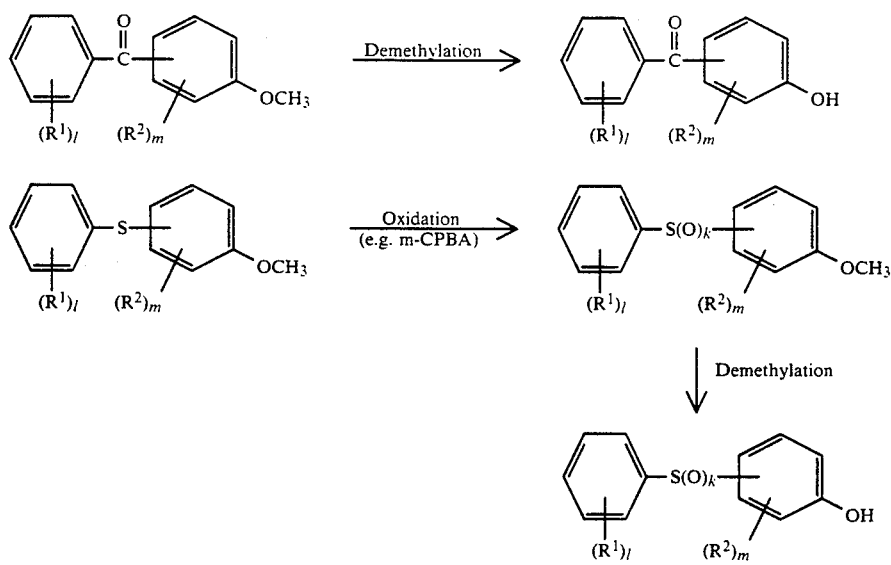

wherein $R^1$, $R^2$, l and m are each as defined above, Ha is a halogen atom and k is an integer of 1 or 2.

Examples of the pyridine derivatives (I) of the present invention are shown in Table 1.

TABLE 1

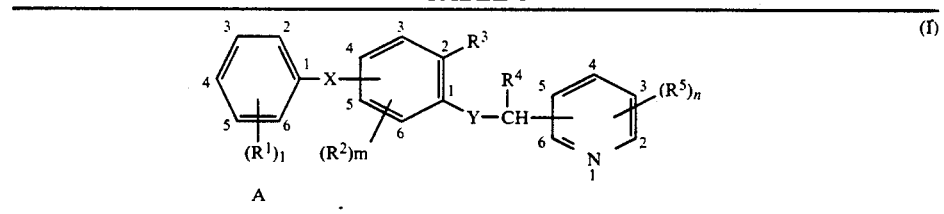

| $(R^1)_l$ | X | $R^2_m$ | $R^3$ | Y | $R^4$ | $(R^5)_n$ | A | B |
|---|---|---|---|---|---|---|---|---|
| H | O | H | Cl | O | H | 2-Cl | 4 | 5 |
| H | O | H | F | O | H | 2-Cl | 4 | 5 |
| H | O | H | Br | O | H | 2-Cl | 4 | 5 |
| H | O | H | $CH_3$ | O | H | 2-Cl | 4 | 5 |
| H | O | H | $C_2H_5$ | O | H | 2-Cl | 4 | 5 |
| H | O | H | $(n)C_3H_7$ | O | H | 2-Cl | 4 | 5 |
| 3-F | O | H | Cl | O | H | 2-Cl | 4 | 5 |
| 3-F | O | H | F | O | H | 2-Cl | 4 | 5 |
| 3-F | O | H | Br | O | H | 2-Cl | 4 | 5 |
| 3-F | O | H | $CH_3$ | O | H | 2-Cl | 4 | 5 |
| 4-F | O | H | Cl | O | H | 2-Cl | 4 | 5 |
| 4-F | O | H | Br | O | H | 2-Cl | 4 | 5 |
| 4-F | O | H | F | O | H | 2-Cl | 4 | 5 |
| 4-F | O | H | $CH_3$ | O | H | 2-Cl | 4 | 5 |
| 2-F | O | H | Cl | O | H | 2-Cl | 4 | 5 |
| 2-F | O | H | Br | O | H | 2-Cl | 4 | 5 |
| 2-F | O | H | F | O | H | 2-Cl | 4 | 5 |
| 2-F | O | H | $CH_3$ | O | H | 2-Cl | 4 | 5 |
| 2-Cl | O | H | Cl | O | H | 2-Cl | 4 | 5 |
| 2-Cl | O | H | Br | O | H | 2-Cl | 4 | 5 |
| 2-Cl | O | H | F | O | H | 2-Cl | 4 | 5 |
| 2-Cl | O | H | $CH_3$ | O | H | 2-Cl | 4 | 5 |
| 3-Cl | O | H | Cl | O | H | 2-Cl | 4 | 5 |
| 3-Cl | O | H | Br | O | H | 2-Cl | 4 | 5 |
| 3-Cl | O | H | F | O | H | 2-Cl | 4 | 5 |
| 3-Cl | O | H | $CH_3$ | O | H | 2-Cl | 4 | 5 |
| 4-Cl | O | H | Cl | O | H | 2-Cl | 4 | 5 |
| 4-Cl | O | H | Br | O | H | 2-Cl | 4 | 5 |
| 4-Cl | O | H | F | O | H | 2-Cl | 4 | 5 |
| 4-Cl | O | H | $CH_3$ | O | H | 2-Cl | 4 | 5 |
| 3-Br | O | H | Cl | O | H | 2-Cl | 4 | 5 |
| 3-Br | O | H | Br | O | H | 2-Cl | 4 | 5 |
| 3-Br | O | H | F | O | H | 2-Cl | 4 | 5 |

TABLE 1-continued (1)

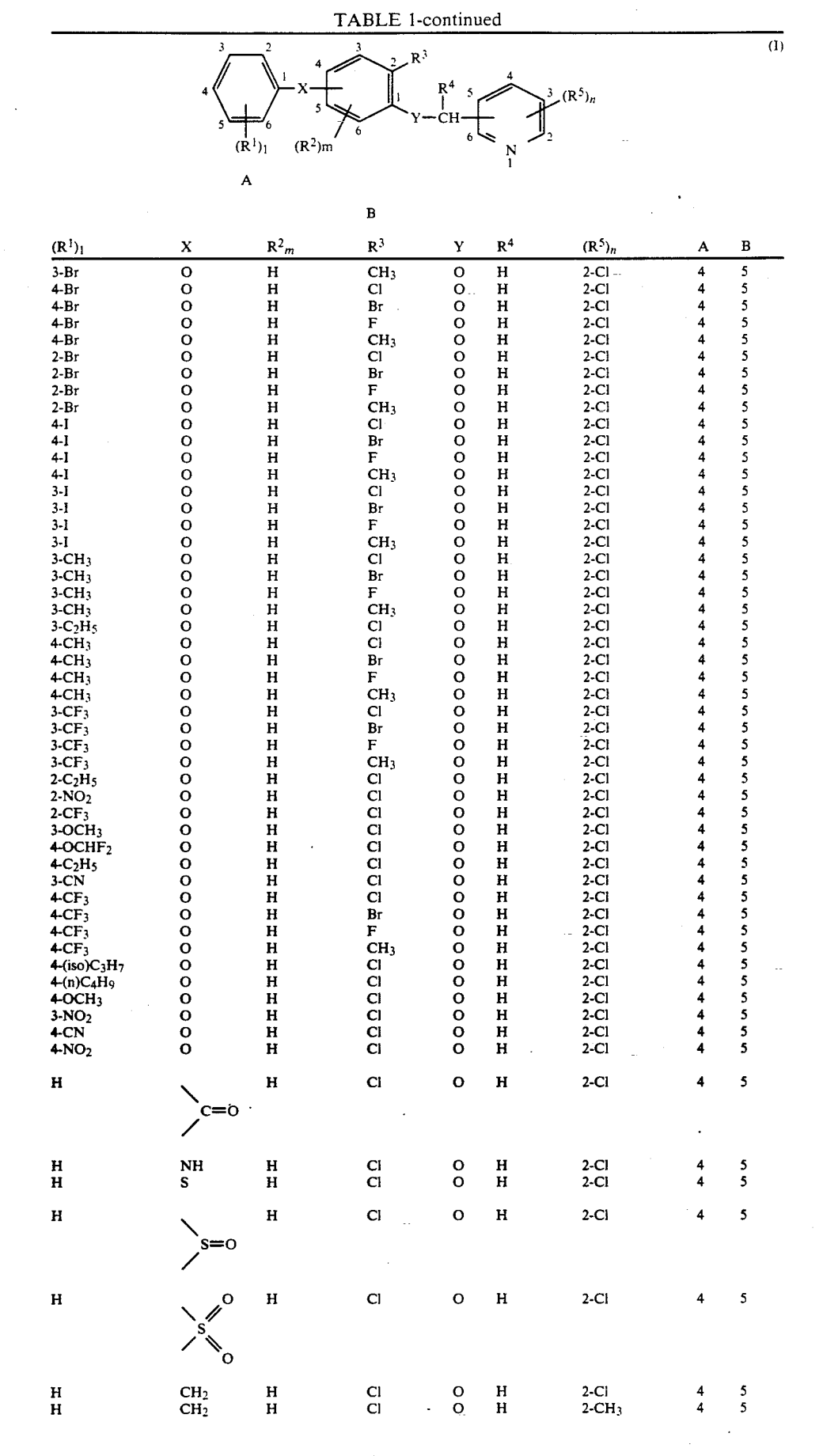

A structure showing: phenyl ring with (R¹)₁ substituents connected via X to a second phenyl ring with R³ and (R²)m substituents, connected via Y—CH(R⁴) to a pyridine ring with (R⁵)n substituents. The first phenyl is labeled A, the second B.

| (R¹)₁ | X | R²ₘ | R³ | Y | R⁴ | (R⁵)ₙ | A | B |
|---|---|---|---|---|---|---|---|---|
| 3-Br | O | H | CH₃ | O | H | 2-Cl | 4 | 5 |
| 4-Br | O | H | Cl | O | H | 2-Cl | 4 | 5 |
| 4-Br | O | H | Br | O | H | 2-Cl | 4 | 5 |
| 4-Br | O | H | F | O | H | 2-Cl | 4 | 5 |
| 4-Br | O | H | CH₃ | O | H | 2-Cl | 4 | 5 |
| 2-Br | O | H | Cl | O | H | 2-Cl | 4 | 5 |
| 2-Br | O | H | Br | O | H | 2-Cl | 4 | 5 |
| 2-Br | O | H | F | O | H | 2-Cl | 4 | 5 |
| 2-Br | O | H | CH₃ | O | H | 2-Cl | 4 | 5 |
| 4-I | O | H | Cl | O | H | 2-Cl | 4 | 5 |
| 4-I | O | H | Br | O | H | 2-Cl | 4 | 5 |
| 4-I | O | H | F | O | H | 2-Cl | 4 | 5 |
| 4-I | O | H | CH₃ | O | H | 2-Cl | 4 | 5 |
| 3-I | O | H | Cl | O | H | 2-Cl | 4 | 5 |
| 3-I | O | H | Br | O | H | 2-Cl | 4 | 5 |
| 3-I | O | H | F | O | H | 2-Cl | 4 | 5 |
| 3-I | O | H | CH₃ | O | H | 2-Cl | 4 | 5 |
| 3-CH₃ | O | H | Cl | O | H | 2-Cl | 4 | 5 |
| 3-CH₃ | O | H | Br | O | H | 2-Cl | 4 | 5 |
| 3-CH₃ | O | H | F | O | H | 2-Cl | 4 | 5 |
| 3-CH₃ | O | H | CH₃ | O | H | 2-Cl | 4 | 5 |
| 3-C₂H₅ | O | H | Cl | O | H | 2-Cl | 4 | 5 |
| 4-CH₃ | O | H | Cl | O | H | 2-Cl | 4 | 5 |
| 4-CH₃ | O | H | Br | O | H | 2-Cl | 4 | 5 |
| 4-CH₃ | O | H | F | O | H | 2-Cl | 4 | 5 |
| 4-CH₃ | O | H | CH₃ | O | H | 2-Cl | 4 | 5 |
| 3-CF₃ | O | H | Cl | O | H | 2-Cl | 4 | 5 |
| 3-CF₃ | O | H | Br | O | H | 2-Cl | 4 | 5 |
| 3-CF₃ | O | H | F | O | H | 2-Cl | 4 | 5 |
| 3-CF₃ | O | H | CH₃ | O | H | 2-Cl | 4 | 5 |
| 2-C₂H₅ | O | H | Cl | O | H | 2-Cl | 4 | 5 |
| 2-NO₂ | O | H | Cl | O | H | 2-Cl | 4 | 5 |
| 2-CF₃ | O | H | Cl | O | H | 2-Cl | 4 | 5 |
| 3-OCH₃ | O | H | Cl | O | H | 2-Cl | 4 | 5 |
| 4-OCHF₂ | O | H | Cl | O | H | 2-Cl | 4 | 5 |
| 4-C₂H₅ | O | H | Cl | O | H | 2-Cl | 4 | 5 |
| 3-CN | O | H | Cl | O | H | 2-Cl | 4 | 5 |
| 4-CF₃ | O | H | Cl | O | H | 2-Cl | 4 | 5 |
| 4-CF₃ | O | H | Br | O | H | 2-Cl | 4 | 5 |
| 4-CF₃ | O | H | F | O | H | 2-Cl | 4 | 5 |
| 4-CF₃ | O | H | CH₃ | O | H | 2-Cl | 4 | 5 |
| 4-(iso)C₃H₇ | O | H | Cl | O | H | 2-Cl | 4 | 5 |
| 4-(n)C₄H₉ | O | H | Cl | O | H | 2-Cl | 4 | 5 |
| 4-OCH₃ | O | H | Cl | O | H | 2-Cl | 4 | 5 |
| 3-NO₂ | O | H | Cl | O | H | 2-Cl | 4 | 5 |
| 4-CN | O | H | Cl | O | H | 2-Cl | 4 | 5 |
| 4-NO₂ | O | H | Cl | O | H | 2-Cl | 4 | 5 |
| H | \C=O/ | H | Cl | O | H | 2-Cl | 4 | 5 |
| H | NH | H | Cl | O | H | 2-Cl | 4 | 5 |
| H | S | H | Cl | O | H | 2-Cl | 4 | 5 |
| H | \S=O/ | H | Cl | O | H | 2-Cl | 4 | 5 |
| H | \S(=O)₂/ | H | Cl | O | H | 2-Cl | 4 | 5 |
| H | CH₂ | H | Cl | O | H | 2-Cl | 4 | 5 |
| H | CH₂ | H | Cl | O | H | 2-CH₃ | 4 | 5 |

TABLE 1-continued (I)

Structure: Phenyl ring A (with $(R^1)_l$ at positions on ring, numbered 1-6) — X — Phenyl ring (with $(R^2)_m$ and $R^3$ at position 2) — Y — CH($R^4$) — Pyridyl ring B (with $(R^5)_n$, N at position 1)

| $(R^1)_l$ | X | $R^2_m$ | $R^3$ | Y | $R^4$ | $(R^5)_n$ | A | B |
|---|---|---|---|---|---|---|---|---|
| H | O | H | Cl | S | H | 2-Cl | 4 | 5 |
| H | O | H | Cl | S | H | 2-CH₃ | 4 | 5 |
| H | O | H | Cl | O | H | 2,6-Cl₂ | 4 | 5 |
| H | O | H | Cl | O | H | 3-Cl | 4 | 5 |
| H | O | H | Cl | O | H | 2,6-Cl₂ | 4 | 5 |
| H | O | H | Cl | O | H | 2-CH₃ | 4 | 5 |
| H | O | H | Br | O | H | 2-CH₃ | 4 | 5 |
| H | O | H | F | O | H | 2-CH₃ | 4 | 5 |
| H | O | H | CH₃ | O | H | 2-CH₃ | 4 | 5 |
| H | O | H | C₂H₅ | O | H | 2-CH₃ | 4 | 5 |
| H | O | H | (n)C₃H₇ | O | H | 2-CH₃ | 4 | 5 |
| 3-F | O | H | Cl | O | H | 2-CH₃ | 4 | 5 |
| 3-F | O | H | Br | O | H | 2-CH₃ | 4 | 5 |
| 3-F | O | H | F | O | H | 2-CH₃ | 4 | 5 |
| 3-F | O | H | CH₃ | O | H | 2-CH₃ | 4 | 5 |
| 4-F | O | H | Cl | O | H | 2-CH₃ | 4 | 5 |
| 4-F | O | H | Br | O | H | 2-CH₃ | 4 | 5 |
| 4-F | O | H | F | O | H | 2-CH₃ | 4 | 5 |
| 4-F | O | H | CH₃ | O | H | 2-CH₃ | 4 | 5 |
| 2-F | O | H | Cl | O | H | 2-CH₃ | 4 | 5 |
| 3-Cl | O | H | Cl | O | H | 2-CH₃ | 4 | 5 |
| 3-Cl | O | H | Br | O | H | 2-CH₃ | 4 | 5 |
| 3-Cl | O | H | F | O | H | 2-CH₃ | 4 | 5 |
| 3-Cl | O | H | CH₃ | O | H | 2-CH₃ | 4 | 5 |
| 4-Cl | O | H | Cl | O | H | 2-CH₃ | 4 | 5 |
| 4-Cl | O | H | Br | O | H | 2-CH₃ | 4 | 5 |
| 4-Cl | O | H | F | O | H | 2-CH₃ | 4 | 5 |
| 4-Cl | O | H | CH₃ | O | H | 2-CH₃ | 4 | 5 |
| 2-Cl | O | H | Cl | O | H | 2-CH₃ | 4 | 5 |
| 2-Br | O | H | Cl | O | H | 2-CH₃ | 4 | 5 |
| 3-Br | O | H | Cl | O | H | 2-CH₃ | 4 | 5 |
| 4-Br | O | H | Cl | O | H | 2-CH₃ | 4 | 5 |
| 4-I | O | H | Cl | O | H | 2-CH₃ | 4 | 5 |
| 4-I | O | H | Br | O | H | 2-CH₃ | 4 | 5 |
| 4-I | O | H | F | O | H | 2-CH₃ | 4 | 5 |
| 4-I | O | H | CH₃ | O | H | 2-CH₃ | 4 | 5 |
| 3-I | O | H | Cl | O | H | 2-CH₃ | 4 | 5 |
| 3-I | O | H | Br | O | H | 2-CH₃ | 4 | 5 |
| 3-I | O | H | F | O | H | 2-CH₃ | 4 | 5 |
| 3-I | O | H | CH₃ | O | H | 2-CH₃ | 4 | 5 |
| 3-CH₃ | O | H | Cl | O | H | 2-CH₃ | 4 | 5 |
| 3-CH₃ | O | H | Br | O | H | 2-CH₃ | 4 | 5 |
| 3-CH₃ | O | H | F | O | H | 2-CH₃ | 4 | 5 |
| 3-CH₃ | O | H | CH₃ | O | H | 2-CH₃ | 4 | 5 |
| 4-CH₃ | O | H | Cl | O | H | 2-CH₃ | 4 | 5 |
| 4-CH₃ | O | H | F | O | H | 2-CH₃ | 4 | 5 |
| 4-CH₃ | O | H | Br | O | H | 2-CH₃ | 4 | 5 |
| 4-CH₃ | O | H | CH₃ | O | H | 2-CH₃ | 4 | 5 |
| 3-CF₃ | O | H | Cl | O | H | 2-CH₃ | 4 | 5 |
| 3-CF₃ | O | H | Br | O | H | 2-CH₃ | 4 | 5 |
| 3-CF₃ | O | H | F | O | H | 2-CH₃ | 4 | 5 |
| 3-CF₃ | O | H | CH₃ | O | H | 2-CH₃ | 4 | 5 |
| 2-CH₃ | O | H | Cl | O | H | 2-CH₃ | 4 | 5 |
| 3-OCH₃ | O | H | Cl | O | H | 2-CH₃ | 4 | 5 |
| 4-CF₃ | O | H | Cl | O | H | 2-CH₃ | 4 | 5 |
| H | O | H | Cl | O | H | 2-Cl | 5 | 5 |
| H | O | H | Br | O | H | 2-Cl | 5 | 5 |
| H | O | H | F | O | H | 2-Cl | 5 | 5 |
| H | O | H | CH₃ | O | H | 2-Cl | 5 | 5 |
| 3-F | O | H | Cl | O | H | 2-Cl | 5 | 5 |
| 3-F | O | H | F | O | H | 2-Cl | 5 | 5 |
| 3-F | O | H | Br | O | H | 2-Cl | 5 | 5 |
| 3-F | O | H | CH₃ | O | H | 2-Cl | 5 | 5 |
| 4-F | O | H | Cl | O | H | 2-Cl | 5 | 5 |
| 2-F | O | H | Cl | O | H | 2-Cl | 5 | 5 |
| 2-Cl | O | H | Cl | O | H | 2-Cl | 5 | 5 |
| 3-Cl | O | H | Cl | O | H | 2-Cl | 5 | 5 |
| 3-Cl | O | H | Br | O | H | 2-Cl | 5 | 5 |
| 3-Cl | O | H | F | O | H | 2-Cl | 5 | 5 |

TABLE 1-continued (I)

| (R¹)₁ | X | R²ₘ | R³ | Y | R⁴ | (R⁵)ₙ | A | B |
|---|---|---|---|---|---|---|---|---|
| 3-Cl | O | H | CH₃ | O | H | 2-Cl | 5 | 5 |
| 4-Cl | O | H | Cl | O | H | 2-Cl | 5 | 5 |
| 4-Br | O | H | Cl | O | H | 2-Cl | 5 | 5 |
| 3-Br | O | H | Cl | O | H | 2-Cl | 5 | 5 |
| 2-Br | O | H | Cl | O | H | 2-Cl | 5 | 5 |
| 3-CH₃ | O | H | Cl | O | H | 2-Cl | 5 | 5 |
| 4-CH₃ | O | H | Cl | O | H | 2-Cl | 5 | 5 |
| 3-CF₃ | O | H | Cl | O | H | 2-Cl | 5 | 5 |
| 2-CH₃ | O | H | Cl | O | H | 2-Cl | 5 | 5 |
| 3-I | O | H | Cl | O | H | 2-Cl | 5 | 5 |
| 4-I | O | H | Cl | O | H | 2-Cl | 5 | 5 |
| 3-OCH₃ | O | H | Cl | O | H | 2-Cl | 5 | 5 |
| 4-OCHF₂ | O | H | Cl | O | H | 2-Cl | 5 | 5 |
| 4-CF₃ | O | H | Cl | O | H | 2-Cl | 5 | 5 |
| H | O | H | Cl | O | H | 2-CH₃ | 5 | 5 |
| 3-F | O | H | Cl | O | H | 2-CH₃ | 5 | 5 |
| 3-F | O | H | Br | O | H | 2-CH₃ | 5 | 5 |
| 3-F | O | H | F | O | H | 2-CH₃ | 5 | 5 |
| 3-F | O | H | CH₃ | O | H | 2-CH₃ | 5 | 5 |
| 3-Cl | O | H | Cl | O | H | 2-CH₃ | 5 | 5 |
| 4-Cl | O | H | Cl | O | H | 2-CH₃ | 5 | 5 |
| 3,5-F₂ | O | H | Cl | O | H | 2-Cl | 4 | 5 |
| 3,5-F₂ | O | H | Br | O | H | 2-Cl | 4 | 5 |
| 3,5-F₂ | O | H | F | O | H | 2-Cl | 4 | 5 |
| 3,5-F₂ | O | H | CH₃ | O | H | 2-Cl | 4 | 5 |
| 2,4-F₂ | O | H | Cl | O | H | 2-Cl | 4 | 5 |
| 2,4-F₂ | O | H | Br | O | H | 2-Cl | 4 | 5 |
| 2,4-F₂ | O | H | F | O | H | 2-Cl | 4 | 5 |
| 2,4-F₂ | O | H | CH₃ | O | H | 2-Cl | 4 | 5 |
| 3,4-F₂ | O | H | Cl | O | H | 2-Cl | 4 | 5 |
| 3,4-F₂ | O | H | Br | O | H | 2-Cl | 4 | 5 |
| 3,4-F₂ | O | H | F | O | H | 2-Cl | 4 | 5 |
| 3,4-F₂ | O | H | CH₃ | O | H | 2-Cl | 4 | 5 |
| 2,6-F₂ | O | H | Cl | O | H | 2-Cl | 4 | 5 |
| 2,6-F₂ | O | H | F | O | H | 2-Cl | 4 | 5 |
| 2,6-F₂ | O | H | Br | O | H | 2-Cl | 4 | 5 |
| 2,6-F₂ | O | H | CH₃ | O | H | 2-Cl | 4 | 5 |
| 2,5-F₂ | O | H | Cl | O | H | 2-Cl | 4 | 5 |
| 2,5-F₂ | O | H | Br | O | H | 2-Cl | 4 | 5 |
| 2,5-F₂ | O | H | F | O | H | 2-Cl | 4 | 5 |
| 2,5-F₂ | O | H | CH₃ | O | H | 2-Cl | 4 | 5 |
| 2,3-F₂ | O | H | Cl | O | H | 2-Cl | 4 | 5 |
| 2,3-F₂ | O | H | Br | O | H | 2-Cl | 4 | 5 |
| 2,3-F₂ | O | H | F | O | H | 2-Cl | 4 | 5 |
| 2,3-F₂ | O | H | CH₃ | O | H | 2-Cl | 4 | 5 |
| 3,4-Cl₂ | O | H | Cl | O | H | 2-Cl | 4 | 5 |
| 3,4-Cl₂ | O | H | Br | O | H | 2-Cl | 4 | 5 |
| 3,4-Cl₂ | O | H | F | O | H | 2-Cl | 4 | 5 |
| 3,4-Cl₂ | O | H | CH₃ | O | H | 2-Cl | 4 | 5 |
| 3,5-Cl₂ | O | H | Cl | O | H | 2-Cl | 4 | 5 |
| 3,5-Cl₂ | O | H | Br | O | H | 2-Cl | 4 | 5 |
| 3,5-Cl₂ | O | H | F | O | H | 2-Cl | 4 | 5 |
| 3,5-Cl₂ | O | H | CH₃ | O | H | 2-Cl | 4 | 5 |
| 2,4-Cl₂ | O | H | Cl | O | H | 2-Cl | 4 | 5 |
| 2,4-Cl₂ | O | H | Br | O | H | 2-Cl | 4 | 5 |
| 2,4-Cl₂ | O | H | F | O | H | 2-Cl | 4 | 5 |
| 2,4-Cl₂ | O | H | CH₃ | O | H | 2-Cl | 4 | 5 |
| 2,5-Cl₂ | O | H | Cl | O | H | 2-Cl | 4 | 5 |
| 2,5-Cl₂ | O | H | Br | O | H | 2-Cl | 4 | 5 |
| 2,5-Cl₂ | O | H | F | O | H | 2-Cl | 4 | 5 |
| 2,5-Cl₂ | O | H | CH₃ | O | H | 2-Cl | 4 | 5 |
| 2,3-Cl₂ | O | H | Cl | O | H | 2-Cl | 4 | 5 |
| 2,3-Cl₂ | O | H | Br | O | H | 2-Cl | 4 | 5 |
| 2,3-Cl₂ | O | H | F | O | H | 2-Cl | 4 | 5 |
| 2,3-Cl₂ | O | H | CH₃ | O | H | 2-Cl | 4 | 5 |
| 3,5-Br₂ | O | H | Cl | O | H | 2-Cl | 4 | 5 |
| 3,5-Br₂ | O | H | F | O | H | 2-Cl | 4 | 5 |
| 3,5-Br₂ | O | H | Br | O | H | 2-Cl | 4 | 5 |
| 3,5-Br₂ | O | H | CH₃ | O | H | 2-Cl | 4 | 5 |

TABLE 1-continued (I)

Structure: Diphenyl ether (ring A) — X — (ring B with R³) — Y — CH(R⁴) — pyridine with (R⁵)ₙ

| (R¹)₁ | X | R²ₘ | R³ | Y | R⁴ | (R⁵)ₙ | A | B |
|---|---|---|---|---|---|---|---|---|
| 2,3-Br₂ | O | H | CH₃ | O | H | 2-Cl | 4 | 5 |
| 2,3-Br₂ | O | H | Cl | O | H | 2-Cl | 4 | 5 |
| 2,3-Br₂ | O | H | Br | O | H | 2-Cl | 4 | 5 |
| 2,3-Br₂ | O | H | F | O | H | 2-Cl | 4 | 5 |
| 2,5-Br₂ | O | H | Cl | O | H | 2-Cl | 4 | 5 |
| 2,5-Br₂ | O | H | Br | O | H | 2-Cl | 4 | 5 |
| 2,5-Br₂ | O | H | F | O | H | 2-Cl | 4 | 5 |
| 2,5-Br₂ | O | H | CH₃ | O | H | 2-Cl | 4 | 5 |
| 3,4-(CH₃)₂ | O | H | Cl | O | H | 2-Cl | 4 | 5 |
| 3,4-(CH₃)₂ | O | H | F | O | H | 2-Cl | 4 | 5 |
| 3,4-(CH₃)₂ | O | H | Br | O | H | 2-Cl | 4 | 5 |
| 3,4-(CH₃)₂ | O | H | CH₃ | O | H | 2-Cl | 4 | 5 |
| 3,5-(CH₃)₂ | O | H | Cl | O | H | 2-Cl | 4 | 5 |
| 3,5-(CH₃)₂ | O | H | Br | O | H | 2-Cl | 4 | 5 |
| 3,5-(CH₃)₂ | O | H | F | O | H | 2-Cl | 4 | 5 |
| 3,5-(CH₃)₂ | O | H | CH₃ | O | H | 2-Cl | 4 | 5 |
| 2,5-(CH₃)₂ | O | H | Cl | O | H | 2-Cl | 4 | 5 |
| 2,5-(CH₃)₂ | O | H | F | O | H | 2-Cl | 4 | 5 |
| 2,5-(CH₃)₂ | O | H | Br | O | H | 2-Cl | 4 | 5 |
| 2,5-(CH₃)₂ | O | H | CH₃ | O | H | 2-Cl | 4 | 5 |
| 2,3-(CH₃)₂ | O | H | Cl | O | H | 2-Cl | 4 | 5 |
| 2,3-(CH₃)₂ | O | H | F | O | H | 2-Cl | 4 | 5 |
| 2,3-(CH₃)₂ | O | H | Br | O | H | 2-Cl | 4 | 5 |
| 2,3-(CH₃)₂ | O | H | CH₃ | O | H | 2-Cl | 4 | 5 |
| 3,5-(CF₃)₂ | O | H | Cl | O | H | 2-Cl | 4 | 5 |
| 3,5-(CF₃)₂ | O | H | F | O | H | 2-Cl | 4 | 5 |
| 3,5-(CF₃)₂ | O | H | Br | O | H | 2-Cl | 4 | 5 |
| 3,5-(CF₃)₂ | O | H | CH₃ | O | H | 2-Cl | 4 | 5 |
| 3,4,5-Cl₃ | O | H | Cl | O | H | 2-Cl | 4 | 5 |
| 3,4,5-Cl₃ | O | H | F | O | H | 2-Cl | 4 | 5 |
| 3,4,5-Cl₃ | O | H | Br | O | H | 2-Cl | 4 | 5 |
| 3,4,5-Cl₃ | O | H | CH₃ | O | H | 2-Cl | 4 | 5 |
| 2-F, 4-Cl | O | H | Cl | O | H | 2-Cl | 4 | 5 |
| 2-F, 4-Cl | O | H | F | O | H | 2-Cl | 4 | 5 |
| 2-F, 4-Cl | O | H | Br | O | H | 2-Cl | 4 | 5 |
| 2-F, 4-Cl | O | H | CH₃ | O | H | 2-Cl | 4 | 5 |
| 2-Cl, 4-Br | O | H | Cl | O | H | 2-Cl | 4 | 5 |
| 2-Cl, 4-Br | O | H | F | O | H | 2-Cl | 4 | 5 |
| 2-Cl, 4-Br | O | H | Br | O | H | 2-Cl | 4 | 5 |
| 2-Cl, 4-Br | O | H | CH₃ | O | H | 2-Cl | 4 | 5 |
| 2-Cl, 4-CH₃ | O | H | Cl | O | H | 2-Cl | 4 | 5 |
| 2-Cl, 4-CH₃ | O | H | F | O | H | 2-Cl | 4 | 5 |
| 2-Cl, 4-CH₃ | O | H | Br | O | H | 2-Cl | 4 | 5 |
| 2-Cl, 4-CH₃ | O | H | CH₃ | O | H | 2-Cl | 4 | 5 |
| 2-F, 4-CH₃ | O | H | Cl | O | H | 2-Cl | 4 | 5 |
| 2-F, 4-CH₃ | O | H | F | O | H | 2-Cl | 4 | 5 |
| 2-F, 4-CH₃ | O | H | Br | O | H | 2-Cl | 4 | 5 |
| 2-F, 4-CH₃ | O | H | CH₃ | O | H | 2-Cl | 4 | 5 |
| 2,4-Br₂ | O | H | Cl | O | H | 2-Cl | 4 | 5 |
| 2,4-Br₂ | O | H | F | O | H | 2-Cl | 4 | 5 |
| 2,4-Br₂ | O | H | Br | O | H | 2-Cl | 4 | 5 |
| 2,4-Br₂ | O | H | CH₃ | O | H | 2-Cl | 4 | 5 |
| 2-F, 4-Br | O | H | Cl | O | H | 2-Cl | 4 | 5 |
| 2-F, 4-Br | O | H | F | O | H | 2-Cl | 4 | 5 |
| 2-F, 4-Br | O | H | Br | O | H | 2-Cl | 4 | 5 |
| 2-F, 4-Br | O | H | CH₃ | O | H | 2-Cl | 4 | 5 |
| 2-Cl, 4-CF₃ | O | H | Cl | O | H | 2-Cl | 4 | 5 |
| 2-Cl, 4-CF₃ | O | H | F | O | H | 2-Cl | 4 | 5 |
| 2-Cl, 4-CF₃ | O | H | Br | O | H | 2-Cl | 4 | 5 |
| 2-Cl, 4-CF₃ | O | H | CH₃ | O | H | 2-Cl | 4 | 5 |
| 2-Cl, 4-F | O | H | Cl | O | H | 2-Cl | 4 | 5 |
| 2-Cl, 4-F | O | H | F | O | H | 2-Cl | 4 | 5 |
| 2-Cl, 4-F | O | H | Br | O | H | 2-Cl | 4 | 5 |
| 2-Cl, 4-F | O | H | CH₃ | O | H | 2-Cl | 4 | 5 |
| 2-CF₃, 4-Cl | O | H | Cl | O | H | 2-Cl | 4 | 5 |
| 2-CF₃, 4-Cl | O | H | F | O | H | 2-Cl | 4 | 5 |
| 2-CF₃, 4-Cl | O | H | Br | O | H | 2-Cl | 4 | 5 |
| 2-CF₃, 4-Cl | O | H | CH₃ | O | H | 2-Cl | 4 | 5 |
| 2-CH₃, 4-Cl | O | H | F | O | H | 2-Cl | 4 | 5 |

TABLE 1-continued (I)

| (R¹)₁ | X | R²ₘ | R³ | Y | R⁴ | (R⁵)ₙ | A | B |
|---|---|---|---|---|---|---|---|---|
| 2-CH₃, 4-Cl | O | H | Cl | O | H | 2-Cl | 4 | 5 |
| 2-CH₃, 4-Cl | O | H | Br | O | H | 2-Cl | 4 | 5 |
| 2-CH₃, 4-Cl | O | H | CH₃ | O | H | 2-Cl | 4 | 5 |
| 2-Br, 4-CH₃ | O | H | Cl | O | H | 2-Cl | 4 | 5 |
| 2-Br, 4-CH₃ | O | H | F | O | H | 2-Cl | 4 | 5 |
| 2-Br, 4-CH₃ | O | H | Br | O | H | 2-Cl | 4 | 5 |
| 2-Br, 4-CH₃ | O | H | CH₃ | O | H | 2-Cl | 4 | 5 |
| 3-F, 4-CH₃ | O | H | Cl | O | H | 2-Cl | 4 | 5 |
| 3-F, 4-CH₃ | O | H | F | O | H | 2-Cl | 4 | 5 |
| 3-F, 4-CH₃ | O | H | Br | O | H | 2-Cl | 4 | 5 |
| 3-F, 4-CH₃ | O | H | CH₃ | O | H | 2-Cl | 4 | 5 |
| 3-Cl, 4-CH₃ | O | H | Cl | O | H | 2-Cl | 4 | 5 |
| 3-Cl, 4-CH₃ | O | H | F | O | H | 2-Cl | 4 | 5 |
| 3-Cl, 4-CH₃ | O | H | Br | O | H | 2-Cl | 4 | 5 |
| 3-Cl, 4-CH₃ | O | H | CH₃ | O | H | 2-Cl | 4 | 5 |
| 3-Br, 4-CH₃ | O | H | F | O | H | 2-Cl | 4 | 5 |
| 3-Br, 4-CH₃ | O | H | Cl | O | H | 2-Cl | 4 | 5 |
| 3-Br, 4-CH₃ | O | H | Br | O | H | 2-Cl | 4 | 5 |
| 3-Br, 4-CH₃ | O | H | CH₃ | O | H | 2-Cl | 4 | 5 |
| 3-CH₃, 4-F | O | H | Cl | O | H | 2-Cl | 4 | 5 |
| 3-CH₃, 4-F | O | H | F | O | H | 2-Cl | 4 | 5 |
| 3-CH₃, 4-F | O | H | Br | O | H | 2-Cl | 4 | 5 |
| 3-CH₃, 4-F | O | H | CH₃ | O | H | 2-Cl | 4 | 5 |
| 3-CH₃, 4-Br | O | H | Cl | O | H | 2-Cl | 4 | 5 |
| 3-CH₃, 4-Br | O | H | F | O | H | 2-Cl | 4 | 5 |
| 3-CH₃, 4-Br | O | H | Br | O | H | 2-Cl | 4 | 5 |
| 3-CH₃, 4-Br | O | H | CH₃ | O | H | 2-Cl | 4 | 5 |
| 3-Cl, 4-F | O | H | Cl | O | H | 2-Cl | 4 | 5 |
| 3-Cl, 4-F | O | H | F | O | H | 2-Cl | 4 | 5 |
| 3-Cl, 4-F | O | H | Br | O | H | 2-Cl | 4 | 5 |
| 3-Cl, 4-F | O | H | CH₃ | O | H | 2-Cl | 4 | 5 |
| 3-F, 4-Cl | O | H | Cl | O | H | 2-Cl | 4 | 5 |
| 3-F, 4-Cl | O | H | F | O | H | 2-Cl | 4 | 5 |
| 3-F, 4-Cl | O | H | Br | O | H | 2-Cl | 4 | 5 |
| 3-F, 4-Cl | O | H | CH₃ | O | H | 2-Cl | 4 | 5 |
| 3-F, 4-Br | O | H | Cl | O | H | 2-Cl | 4 | 5 |
| 3-F, 4-Br | O | H | F | O | H | 2-Cl | 4 | 5 |
| 3-F, 4-Br | O | H | Br | O | H | 2-Cl | 4 | 5 |
| 3-F, 4-Br | O | H | CH₃ | O | H | 2-Cl | 4 | 5 |
| 3-Cl, 4-Br | O | H | Cl | O | H | 2-Cl | 4 | 5 |
| 3-Cl, 4-Br | O | H | F | O | H | 2-Cl | 4 | 5 |
| 3-Cl, 4-Br | O | H | Br | O | H | 2-Cl | 4 | 5 |
| 3-Cl, 4-Br | O | H | CH₃ | O | H | 2-Cl | 4 | 5 |
| 3-CF₃, 4-Cl | O | H | Cl | O | H | 2-Cl | 4 | 5 |
| 3-CF₃, 4-Cl | O | H | F | O | H | 2-Cl | 4 | 5 |
| 3-CF₃, 4-Cl | O | H | Br | O | H | 2-Cl | 4 | 5 |
| 3-CF₃, 4-Cl | O | H | CH₃ | O | H | 2-Cl | 4 | 5 |
| 3-NO₂, 4-Cl | O | H | F | O | H | 2-Cl | 4 | 5 |
| 3-NO₂, 4-Cl | O | H | Cl | O | H | 2-Cl | 4 | 5 |
| 3-NO₂, 4-Cl | O | H | Br | O | H | 2-Cl | 4 | 5 |
| 3-NO₂, 4-Cl | O | H | CH₃ | O | H | 2-Cl | 4 | 5 |
| 2-Cl, 5-CH₃ | O | H | Cl | O | H | 2-Cl | 4 | 5 |
| 2-Cl, 5-CH₃ | O | H | F | O | H | 2-Cl | 4 | 5 |
| 2-Cl, 5-CH₃ | O | H | Br | O | H | 2-Cl | 4 | 5 |
| 2-Cl, 5-CH₃ | O | H | CH₃ | O | H | 2-Cl | 4 | 5 |
| 2-F, 5-CH₃ | O | H | Cl | O | H | 2-Cl | 4 | 5 |
| 2-F, 5-CH₃ | O | H | F | O | H | 2-Cl | 4 | 5 |
| 2-F, 5-CH₃ | O | H | Br | O | H | 2-Cl | 4 | 5 |
| 2-F, 5-CH₃ | O | H | CH₃ | O | H | 2-Cl | 4 | 5 |
| 3-CH₃, 4-Cl | O | H | F | O | H | 2-Cl | 4 | 5 |
| 3-CH₃, 4-Cl | O | H | Cl | O | H | 2-Cl | 4 | 5 |
| 3-CH₃, 4-Cl | O | H | Br | O | H | 2-Cl | 4 | 5 |
| 3-CH₃, 4-Cl | O | H | CH₃ | O | H | 2-Cl | 4 | 5 |
| 3,5-(CH₃)₂, 4-Cl | O | H | F | O | H | 2-Cl | 4 | 5 |
| 3,5-(CH₃)₂, 4-Cl | O | H | Cl | O | H | 2-Cl | 4 | 5 |
| 3,5-(CH₃)₂, 4-Cl | O | H | Br | O | H | 2-Cl | 4 | 5 |
| 3,5-(CH₃)₂, 4-Cl | O | H | CH₃ | O | H | 2-Cl | 4 | 5 |
| 2,3,4-Cl₃ | O | H | Cl | O | H | 2-Cl | 4 | 5 |
| 2,3,4-Cl₃ | O | H | F | O | H | 2-Cl | 4 | 5 |

TABLE 1-continued (I)

A structural formula with two phenyl rings and a pyridine ring: Ring A (phenyl with (R¹)₁ substituents) is connected via X to Ring B (phenyl with R² and R³ substituents, numbered 1-6), which is connected via Y-CH(R⁴) to a pyridine ring (with (R⁵)ₙ substituents).

| (R¹)₁ | X | R²ₘ | R³ | Y | R⁴ | (R⁵)ₙ | A | B |
|---|---|---|---|---|---|---|---|---|
| 2,3,4-Cl₃ | O | H | Br | O | H | 2-Cl | 4 | 5 |
| 2,3,4-Cl₃ | O | H | CH₃ | O | H | 2-Cl | 4 | 5 |
| 2,4,5-Cl₃ | O | H | Cl | O | H | 2-Cl | 4 | 5 |
| 2,4,5-Cl₃ | O | H | F | O | H | 2-Cl | 4 | 5 |
| 2,4,5-Cl₃ | O | H | Br | O | H | 2-Cl | 4 | 5 |
| 2,4,5-Cl₃ | O | H | CH₃ | O | H | 2-Cl | 4 | 5 |
| 2,4,6-Cl₃ | O | H | Cl | O | H | 2-Cl | 4 | 5 |
| 2,4-Cl₂, 3,5-(CH₃)₂ | O | H | Cl | O | H | 2-Cl | 4 | 5 |
| 2,3,5,6-F₄ | O | H | Cl | O | H | 2-Cl | 4 | 5 |
| 2,3,4,5,6-F₅ | O | H | Cl | O | H | 2-Cl | 4 | 5 |
| 3,5-F₂ | O | H | Cl | O | H | 2-CH₃ | 4 | 5 |
| 3,5-F₂ | O | H | F | O | H | 2-CH₃ | 4 | 5 |
| 3,5-F₂ | O | H | Br | O | H | 2-CH₃ | 4 | 5 |
| 3,5-F₂ | O | H | CH₃ | O | H | 2-CH₃ | 4 | 5 |
| 3,4-Cl₂ | O | H | F | O | H | 2-CH₃ | 4 | 5 |
| 3,4-Cl₂ | O | H | Cl | O | H | 2-CH₃ | 4 | 5 |
| 3,4-Cl₂ | O | H | Br | O | H | 2-CH₃ | 4 | 5 |
| 3,4-Cl₂ | O | H | CH₃ | O | H | 2-CH₃ | 4 | 5 |
| 3,5-Cl₂ | O | H | Cl | O | H | 2-CH₃ | 4 | 5 |
| 3,5-Cl₂ | O | H | F | O | H | 2-CH₃ | 4 | 5 |
| 3,5-Cl₂ | O | H | Br | O | H | 2-CH₃ | 4 | 5 |
| 3,5-Cl₂ | O | H | CH₃ | O | H | 2-CH₃ | 4 | 5 |
| 2,4-F₂ | O | H | Cl | O | H | 2-CH₃ | 4 | 5 |
| 2,4-F₂ | O | H | Br | O | H | 2-CH₃ | 4 | 5 |
| 2,4-F₂ | O | H | F | O | H | 2-CH₃ | 4 | 5 |
| 2,4-F₂ | O | H | CH₃ | O | H | 2-CH₃ | 4 | 5 |
| 3,4-F₂ | O | H | Cl | O | H | 2-CH₃ | 4 | 5 |
| 3,4-F₂ | O | H | F | O | H | 2-CH₃ | 4 | 5 |
| 3,4-F₂ | O | H | Br | O | H | 2-CH₃ | 4 | 5 |
| 3,4-F₂ | O | H | CH₃ | O | H | 2-CH₃ | 4 | 5 |
| 2,4-Cl₂ | O | H | Cl | O | H | 2-CH₃ | 4 | 5 |
| 2,4-Cl₂ | O | H | F | O | H | 2-CH₃ | 4 | 5 |
| 2,4-Cl₂ | O | H | Br | O | H | 2-CH₃ | 4 | 5 |
| 2,4-Cl₂ | O | H | CH₃ | O | H | 2-CH₃ | 4 | 5 |
| 3,5-(CH₃)₂ | O | H | Cl | O | H | 2-CH₃ | 4 | 5 |
| 3,5-(CH₃)₂ | O | H | F | O | H | 2-CH₃ | 4 | 5 |
| 3,5-(CH₃)₂ | O | H | Br | O | H | 2-CH₃ | 4 | 5 |
| 3,5-(CH₃)₂ | O | H | CH₃ | O | H | 2-CH₃ | 4 | 5 |
| 3,4-(CH₃)₂ | O | H | Cl | O | H | 2-CH₃ | 4 | 5 |
| 3,4-(CH₃)₂ | O | H | F | O | H | 2-CH₃ | 4 | 5 |
| 3,4-(CH₃)₂ | O | H | Br | O | H | 2-CH₃ | 4 | 5 |
| 3,4-(CH₃)₂ | O | H | CH₃ | O | H | 2-CH₃ | 4 | 5 |
| 3,5-Br₂ | O | H | Cl | O | H | 2-CH₃ | 4 | 5 |
| 2,6-F₂ | O | H | Cl | O | H | 2-CH₃ | 4 | 5 |
| 2,5-Cl₂ | O | H | Cl | O | H | 2-CH₃ | 4 | 5 |
| 2,5-F₂ | O | H | Cl | O | H | 2-CH₃ | 4 | 5 |
| 2,5-F₂ | O | H | F | O | H | 2-CH₃ | 4 | 5 |
| 2,5-F₂ | O | H | Br | O | H | 2-CH₃ | 4 | 5 |
| 2,5-F₂ | O | H | CH₃ | O | H | 2-CH₃ | 4 | 5 |
| 2,3-F₂ | O | H | Cl | O | H | 2-CH₃ | 4 | 5 |
| 2,3-F₂ | O | H | F | O | H | 2-CH₃ | 4 | 5 |
| 2,3-F₂ | O | H | Br | O | H | 2-CH₃ | 4 | 5 |
| 2,3-F₂ | O | H | CH₃ | O | H | 2-CH₃ | 4 | 5 |
| 2,5-(CH₃)₂ | O | H | Cl | O | H | 2-CH₃ | 4 | 5 |
| 2,3-Cl₂ | O | H | Cl | O | H | 2-CH₃ | 4 | 5 |
| 2,3-(CH₃)₂ | O | H | Cl | O | H | 2-CH₃ | 4 | 5 |
| 2,3-Br₂ | O | H | Cl | O | H | 2-CH₃ | 4 | 5 |
| 2,5-Br₂ | O | H | Cl | O | H | 2-CH₃ | 4 | 5 |
| 3,5-(CF₃)₂ | O | H | Cl | O | H | 2-CH₃ | 4 | 5 |
| 3,4,5-Cl₃ | O | H | Cl | O | H | 2-CH₃ | 4 | 5 |
| 2-F, 4-Cl | O | H | Cl | O | H | 2-CH₃ | 4 | 5 |
| 2-Cl, 4-Br | O | H | Cl | O | H | 2-CH₃ | 4 | 5 |
| 2-Cl, 4-CH₃ | O | H | Cl | O | H | 2-CH₃ | 4 | 5 |
| 2-F, 4-CH₃ | O | H | Cl | O | H | 2-CH₃ | 4 | 5 |
| 2,4-Br₂ | O | H | Cl | O | H | 2-CH₃ | 4 | 5 |
| 2-F, 4-Br | O | H | Cl | O | H | 2-CH₃ | 4 | 5 |
| 2-Cl, 4-CF₃ | O | H | Cl | O | H | 2-CH₃ | 4 | 5 |
| 2-Cl, 4-F | O | H | Cl | O | H | 2-CH₃ | 4 | 5 |

TABLE 1-continued

| (R¹)₁ | X | R²ₘ | R³ | Y | R⁴ | (R⁵)ₙ | A | B |
|---|---|---|---|---|---|---|---|---|
| 2-CF₃, 4-Cl | O | H | Cl | O | H | 2-CH₃ | 4 | 5 |
| 2-CH₃, 4-Cl | O | H | Cl | O | H | 2-CH₃ | 4 | 5 |
| 2-Br, 4-CH₃ | O | H | Cl | O | H | 2-CH₃ | 4 | 5 |
| 3-F, 4-CH₃ | O | H | Cl | O | H | 2-CH₃ | 4 | 5 |
| 3-F, 4-CH₃ | O | H | F | O | H | 2-CH₃ | 4 | 5 |
| 3-F, 4-CH₃ | O | H | Br | O | H | 2-CH₃ | 4 | 5 |
| 3-F, 4-CH₃ | O | H | CH₃ | O | H | 2-CH₃ | 4 | 5 |
| 3-Cl, 4-CH₃ | O | H | F | O | H | 2-CH₃ | 4 | 5 |
| 3-Cl, 4-CH₃ | O | H | Cl | O | H | 2-CH₃ | 4 | 5 |
| 3-Cl, 4-CH₃ | O | H | Br | O | H | 2-CH₃ | 4 | 5 |
| 3-Cl, 4-CH₃ | O | H | CH₃ | O | H | 2-CH₃ | 4 | 5 |
| 3-Br, 4-CH₃ | O | H | Cl | O | H | 2-CH₃ | 4 | 5 |
| 3-CH₃, 4-F | O | H | Cl | O | H | 2-CH₃ | 4 | 5 |
| 3-CH₃, 4-Br | O | H | Cl | O | H | 2-CH₃ | 4 | 5 |
| 3-Cl, 4-F | O | H | Cl | O | H | 2-CH₃ | 4 | 5 |
| 3-Cl, 4-F | O | H | Br | O | H | 2-CH₃ | 4 | 5 |
| 3-Cl, 4-F | O | H | F | O | H | 2-CH₃ | 4 | 5 |
| 3-Cl, 4-F | O | H | CH₃ | O | H | 2-CH₃ | 4 | 5 |
| 3-F, 4-Cl | O | H | Cl | O | H | 2-CH₃ | 4 | 5 |
| 3-F, 4-Cl | O | H | F | O | H | 2-CH₃ | 4 | 5 |
| 3-F, 4-Cl | O | H | Br | O | H | 2-CH₃ | 4 | 5 |
| 3-F, 4-Cl | O | H | CH₃ | O | H | 2-CH₃ | 4 | 5 |
| 3-F, 4-Br | O | H | Cl | O | H | 2-CH₃ | 4 | 5 |
| 3-F, 4-Br | O | H | F | O | H | 2-CH₃ | 4 | 5 |
| 3-F, 4-Br | O | H | Br | O | H | 2-CH₃ | 4 | 5 |
| 3-F, 4-Br | O | H | CH₃ | O | H | 2-CH₃ | 4 | 5 |
| 3-Cl, 4-Br | O | H | F | O | H | 2-CH₃ | 4 | 5 |
| 3-Cl, 4-Br | O | H | Cl | O | H | 2-CH₃ | 4 | 5 |
| 3-Cl, 4-Br | O | H | Br | O | H | 2-CH₃ | 4 | 5 |
| 3-Cl, 4-Br | O | H | CH₃ | O | H | 2-CH₃ | 4 | 5 |
| 3-CF₃, 4-Cl | O | H | Cl | O | H | 2-CH₃ | 4 | 5 |
| 2-Cl, 5-CH₃ | O | H | Cl | O | H | 2-CH₃ | 4 | 5 |
| 2-F, 5-CH₃ | O | H | Cl | O | H | 2-CH₃ | 4 | 5 |
| 3-CH₃, 4-Cl | O | H | Cl | O | H | 2-CH₃ | 4 | 5 |
| 3-CH₃, 4-Cl | O | H | F | O | H | 2-CH₃ | 4 | 5 |
| 3-CH₃, 4-Cl | O | H | Br | O | H | 2-CH₃ | 4 | 5 |
| 3-CH₃, 4-Cl | O | H | CH₃ | O | H | 2-CH₃ | 4 | 5 |
| 3,5-(CH₃)₂, 4-Cl | O | H | Cl | O | H | 2-CH₃ | 4 | 5 |
| 2,3,4-Cl₃ | O | H | Cl | O | H | 2-CH₃ | 4 | 5 |
| 2,4,5-Cl₃ | O | H | Cl | O | H | 2-CH₃ | 4 | 5 |
| 2,4,5-Cl₃ | O | H | F | O | H | 2-CH₃ | 4 | 5 |
| 2,4,5-Cl₃ | O | H | Br | O | H | 2-CH₃ | 4 | 5 |
| 2,4,5-Cl₃ | O | H | CH₃ | O | H | 2-CH₃ | 4 | 5 |
| 3,5-F₂ | O | H | Cl | O | H | 2-CH₃ | 5 | 5 |
| 3,4-Cl₂ | O | H | Cl | O | H | 2-CH₃ | 5 | 5 |
| 3,5-Cl₂ | O | H | Cl | O | H | 2-CH₃ | 5 | 5 |
| 2,4-F₂ | O | H | Cl | O | H | 2-CH₃ | 5 | 5 |
| 3,4-F₂ | O | H | Cl | O | H | 2-CH₃ | 5 | 5 |
| 2,4-Cl₂ | O | H | Cl | O | H | 2-CH₃ | 5 | 5 |
| 3,4-(CH₃)₂ | O | H | Cl | O | H | 2-CH₃ | 5 | 5 |
| 3,5-(CH₃)₂ | O | H | Cl | O | H | 2-CH₃ | 5 | 5 |
| 3,5-Br₂ | O | H | Cl | O | H | 2-CH₃ | 5 | 5 |
| 2,6-F₂ | O | H | Cl | O | H | 2-CH₃ | 5 | 5 |
| 2,5-Cl₂ | O | H | Cl | O | H | 2-CH₃ | 5 | 5 |
| 2,5-F₂ | O | H | Cl | O | H | 2-CH₃ | 5 | 5 |
| 2,5-(CH₃)₂ | O | H | Cl | O | H | 2-CH₃ | 5 | 5 |
| 2,3-F₂ | O | H | Cl | O | H | 2-CH₃ | 5 | 5 |
| 2,3-Cl₂ | O | H | Cl | O | H | 2-CH₃ | 5 | 5 |
| 2,3-(CH₃)₂ | O | H | Cl | O | H | 2-CH₃ | 5 | 5 |
| 3,4-Br₂ | O | H | Cl | O | H | 2-CH₃ | 5 | 5 |
| 2,5-Br₂ | O | H | Cl | O | H | 2-CH₃ | 5 | 5 |
| 2-F, 4-Cl | O | H | Cl | O | H | 2-CH₃ | 5 | 5 |
| 2-Cl, 4-Br | O | H | Cl | O | H | 2-CH₃ | 5 | 5 |
| 2-Cl, 4-CH₃ | O | H | Cl | O | H | 2-CH₃ | 5 | 5 |
| 3-F, 4-CH₃ | O | H | Cl | O | H | 2-CH₃ | 5 | 5 |
| 2,4-Br₂ | O | H | Cl | O | H | 2-CH₃ | 5 | 5 |
| 2-F, 4-Br | O | H | Cl | O | H | 2-CH₃ | 5 | 5 |
| 2-Cl, 4-CF₃ | O | H | Cl | O | H | 2-CH₃ | 5 | 5 |
| 2-Cl, 4-F | O | H | Cl | O | H | 2-CH₃ | 5 | 5 |

TABLE 1-continued (1)

[Structure: Ar(R¹)₁–X–Ar(R²)ₘ(R³)–Y–CH(R⁴)–Pyridine(R⁵)ₙ, with ring A and ring B labeled]

| (R¹)₁ | X | R²ₘ | R³ | Y | R⁴ | (R⁵)ₙ | A | B |
|---|---|---|---|---|---|---|---|---|
| 2-CF₃, 4-Cl | O | H | Cl | O | H | 2-CH₃ | 5 | 5 |
| 2-CH₃, 4-Cl | O | H | Cl | O | H | 2-CH₃ | 5 | 5 |
| 2-Br, 4-CH₃ | O | H | Cl | O | H | 2-CH₃ | 5 | 5 |
| 3-F, 4-CH₃ | O | H | Cl | O | H | 2-CH₃ | 5 | 5 |
| 3-Cl, 4-CH₃ | O | H | Cl | O | H | 2-CH₃ | 5 | 5 |
| 3-Br, 4-CH₃ | O | H | Cl | O | H | 2-CH₃ | 5 | 5 |
| 3-CH₃, 4-F | O | H | Cl | O | H | 2-CH₃ | 5 | 5 |
| 3-CH₃, 4-Br | O | H | Cl | O | H | 2-CH₃ | 5 | 5 |
| 3-Cl, 4-F | O | H | Cl | O | H | 2-CH₃ | 5 | 5 |
| 3-F, 4-Cl | O | H | Cl | O | H | 2-CH₃ | 5 | 5 |
| 3-F, 4-Br | O | H | Cl | O | H | 2-CH₃ | 5 | 5 |
| 3-Cl, 4-Br | O | H | Cl | O | H | 2-CH₃ | 5 | 5 |
| 3-CF₃, 4-Cl | O | H | Cl | O | H | 2-CH₃ | 5 | 5 |
| 2-Cl, 5-CH₃ | O | H | Cl | O | H | 2-CH₃ | 5 | 5 |
| 2-F, 5-CH₃ | O | H | Cl | O | H | 2-CH₃ | 5 | 5 |
| 3-CH₃, 4-Cl | O | H | Cl | O | H | 2-CH₃ | 5 | 5 |
| 3,5-(CH₃)₂, 4-Cl | O | H | Cl | O | H | 2-CH₃ | 5 | 5 |
| 3,4,5-Cl₃ | O | H | Cl | O | H | 2-CH₃ | 5 | 5 |
| 2,4,5-Cl₃ | O | H | Cl | O | H | 2-CH₃ | 5 | 5 |
| 2,4,6-Cl₃ | O | H | Cl | O | H | 2-CH₃ | 5 | 5 |
| H | O | 6-Cl | Cl | O | H | 2-Cl | 4 | 5 |
| H | O | 6-F | Cl | O | H | 2-Cl | 4 | 5 |
| H | O | 3,4-Cl₂ | Cl | O | H | 2-Cl | 4 | 5 |
| H | O | 3,4-(CH₃)₂ | Cl | O | H | 2-Cl | 4 | 5 |
| H | O | 3-Cl | Cl | O | H | 2-Cl | 4 | 5 |
| H | O | H | Cl | O | CH₃ | 2-Cl | 4 | 5 |
| H | O | H | Cl | O | C₂H₅ | 2-Cl | 4 | 5 |
| H | O | H | Cl | O | H | 2-F | 4 | 5 |
| H | O | H | Cl | O | H | 2-Br | 4 | 5 |
| H | O | H | Cl | O | H | 2-CF₃ | 4 | 5 |
| H | O | H | Cl | O | H | 2-C₂H₅ | 4 | 5 |
| H | O | H | Cl | O | H | 2-(iso)-C₃H₇ | 4 | 5 |
| H | O | H | Cl | O | H | 2-(n)-C₃H₇ | 4 | 5 |
| H | O | H | Cl | O | H | 2-I | 4 | 5 |
| H | O | H | Cl | O | H | 2-I | 5 | 5 |
| 3-F | O | H | Cl | O | H | 2-I | 4 | 5 |
| 3,5-F₂ | O | H | Cl | O | H | 2-I | 4 | 5 |
| 3,4-Cl₂ | O | H | Cl | O | H | 2-I | 4 | 5 |
| 3-CH₃ | O | H | Cl | O | H | 2-I | 4 | 5 |
| H | O | H | Cl | O | H | 2-OCH₃ | 4 | 5 |
| H | O | H | Cl | O | H | 2-OC₂H₅ | 4 | 5 |
| H | O | H | Cl | O | H | 2-OCF₃ | 4 | 5 |
| H | O | H | Cl | O | H | 2-OCHF₂ | 4 | 5 |
| H | O | 5-Cl | Cl | O | H | 2-Cl | 4 | 5 |
| 3-F | O | 5-Cl | Cl | O | H | 2-Cl | 4 | 5 |
| 3,5-F₂ | O | 5-Cl | Cl | O | H | 2-Cl | 4 | 5 |
| 3-Cl | O | 5-Cl | Cl | O | H | 2-Cl | 4 | 5 |
| 3,4-Cl₂ | O | 5-Cl | Cl | O | H | 2-Cl | 4 | 5 |
| 4-Cl | O | 5-Cl | Cl | O | H | 2-Cl | 4 | 5 |
| 3,5-Cl₂ | O | 5-Cl | Cl | O | H | 2-Cl | 4 | 5 |
| 2,4-F₂ | O | 5-Cl | Cl | O | H | 2-Cl | 4 | 5 |
| 3,4-F₂ | O | 5-Cl | Cl | O | H | 2-Cl | 4 | 5 |
| 4-F | O | 5-Cl | Cl | O | H | 2-Cl | 4 | 5 |
| 3-CH₃ | O | 5-Cl | Cl | O | H | 2-Cl | 4 | 5, |
| 3,4-(CH₃)₂ | O | 5-Cl | Cl | O | H | 2-Cl | 4 | 5 |
| 3-F, 4-CH₃ | O | 5-Cl | Cl | O | H | 2-Cl | 4 | 5 |
| 3-F, 4-Cl | O | 5-Cl | Cl | O | H | 2-Cl | 4 | 5 |
| 3-CH₃, 4-Cl | O | 5-Cl | Cl | O | H | 2-Cl | 4 | 5 |
| 2,5-F₂ | O | 5-Cl | Cl | O | H | 2-Cl | 4 | 5 |
| 3,4-F₂ | O | 5-Cl | Cl | O | H | 2-Cl | 4 | 5 |
| 3-CH₃, 4-Cl | O | 5-Cl | Cl | O | H | 2-Cl | 4 | 5 |
| H | O | 5-Br | Cl | O | H | 2-Cl | 4 | 5 |
| 3-F | O | 5-Br | Cl | O | H | 2-Cl | 4 | 5 |
| 3,5-F₂ | O | 5-Br | Cl | O | H | 2-Cl | 4 | 5 |
| 3-Cl | O | 5-Br | Cl | O | H | 2-Cl | 4 | 5 |
| 3,4-Cl₂ | O | 5-Br | Cl | O | H | 2-Cl | 4 | 5 |
| 4-Cl | O | 5-Br | Cl | O | H | 2-Cl | 4 | 5 |
| 3,5-Cl₂ | O | 5-Br | Cl | O | H | 2-Cl | 4 | 5 |
| 2,4-F₂ | O | 5-Br | Cl | O | H | 2-Cl | 4 | 5 |

TABLE 1-continued (I)

Structure: (R¹)ₗ-phenyl-X-phenyl(R²)ₘ,R³-Y-CH(R⁴)-pyridine(R⁵)ₙ with ring A and ring B

| (R¹)ₗ | X | R²ₘ | R³ | Y | R⁴ | (R⁵)ₙ | A | B |
|---|---|---|---|---|---|---|---|---|
| 3,4-F₂ | O | 5-Br | Cl | O | H | 2-Cl | 4 | 5 |
| 4-F | O | 5-Br | Cl | O | H | 2-Cl | 4 | 5 |
| 3-CH₃ | O | 5-Br | Cl | O | H | 2-Cl | 4 | 5 |
| 3,4-(CH₃)₂ | O | 5-Br | Cl | O | H | 2-Cl | 4 | 5 |
| 3,5-(CH₃)₂ | O | 5-Br | Cl | O | H | 2-Cl | 4 | 5 |
| 3-F, 4-CH₃ | O | 5-Br | Cl | O | H | 2-Cl | 4 | 5 |
| 3-Cl, 4-CH₃ | O | 5-Br | Cl | O | H | 2-Cl | 4 | 5 |
| 3-F, 4-Cl | O | 5-Br | Cl | O | H | 2-Cl | 4 | 5 |
| 3-CH₃, 4-Cl | O | 5-Br | Cl | O | H | 2-Cl | 4 | 5 |
| 2,5-F₂ | O | 5-Br | Cl | O | H | 2-Cl | 4 | 5 |
| 2,3-F₂ | O | 5-Br | Cl | O | H | 2-Cl | 4 | 5 |
| 3-CH₃, 4-Cl | O | 5-Br | Cl | O | H | 2-Cl | 4 | 5 |
| H | O | 5-F | Cl | O | H | 2-Cl | 4 | 5 |
| 3-F | O | 5-F | Cl | O | H | 2-Cl | 4 | 5 |
| 3,5-F₂ | O | 5-F | Cl | O | H | 2-Cl | 4 | 5 |
| 3-Cl | O | 5-F | Cl | O | H | 2-Cl | 4 | 5 |
| 3,4-Cl₂ | O | 5-F | Cl | O | H | 2-Cl | 4 | 5 |
| 4-Cl | O | 5-F | Cl | O | H | 2-Cl | 4 | 5 |
| 3,5-Cl₂ | O | 5-F | Cl | O | H | 2-Cl | 4 | 5 |
| 2,4-F₂ | O | 5-F | Cl | O | H | 2-Cl | 4 | 5 |
| 3,4-F₂ | O | 5-F | Cl | O | H | 2-Cl | 4 | 5 |
| 4-F | O | 5-F | Cl | O | H | 2-Cl | 4 | 5 |
| 3-CH₃ | O | 5-F | Cl | O | H | 2-Cl | 4 | 5 |
| 3,4-(CH₃)₂ | O | 5-F | Cl | O | H | 2-Cl | 4 | 5 |
| 3,5-(CH₃)₂ | O | 5-F | Cl | O | H | 2-Cl | 4 | 5 |
| 3-F, 4-CH₃ | O | 5-F | Cl | O | H | 2-Cl | 4 | 5 |
| 3-F, 4-Cl | O | 5-F | Cl | O | H | 2-Cl | 4 | 5 |
| 3-CH₃, 4-Cl | O | 5-F | Cl | O | H | 2-Cl | 4 | 5 |
| 2,5-F₂ | O | 5-F | Cl | O | H | 2-Cl | 4 | 5 |
| H | O | 5-CH₃ | Cl | O | H | 2-Cl | 4 | 5 |
| 3-F | O | 5-CH₃ | Cl | O | H | 2-Cl | 4 | 5 |
| 3,5-F₂ | O | 5-CH₃ | Cl | O | H | 2-Cl | 4 | 5 |
| 3-Cl | O | 5-CH₃ | Cl | O | H | 2-Cl | 4 | 5 |
| 3,4-Cl₂ | O | 5-CH₃ | Cl | O | H | 2-Cl | 4 | 5 |
| 4-Cl | O | 5-CH₃ | Cl | O | H | 2-Cl | 4 | 5 |
| 3,5-Cl₂ | O | 5-CH₃ | Cl | O | H | 2-Cl | 4 | 5 |
| 2,4-F₂ | O | 5-CH₃ | Cl | O | H | 2-Cl | 4 | 5 |
| 3,4-F₂ | O | 5-CH₃ | Cl | O | H | 2-Cl | 4 | 5 |
| 4-F | O | 5-CH₃ | Cl | O | H | 2-Cl | 4 | 5 |
| 3-CH₃ | O | 5-CH₃ | Cl | O | H | 2-Cl | 4 | 5 |
| 3,4-(CH₃)₂ | O | 5-CH₃ | Cl | O | H | 2-Cl | 4 | 5 |
| 3,5-(CH₃)₂ | O | 5-CH₃ | Cl | O | H | 2-Cl | 4 | 5 |
| 3-F, 4-CH₃ | O | 5-CH₃ | Cl | O | H | 2-Cl | 4 | 5 |
| 3-Cl, 4-CH₃ | O | 5-CH₃ | Cl | O | H | 2-Cl | 4 | 5 |
| 3-F, 4-Cl | O | 5-CH₃ | Cl | O | H | 2-Cl | 4 | 5 |
| 3-CH₃, 4-Cl | O | 5-CH₃ | Cl | O | H | 2-Cl | 4 | 5 |
| 2,5-F₂ | O | 5-CH₃ | Cl | O | H | 2-Cl | 4 | 5 |
| 2,3-F₂ | O | 5-CH₃ | Cl | O | H | 2-Cl | 4 | 5 |
| 3-CH₃, 4-Cl | O | 5-CH₃ | Cl | O | H | 2-Cl | 4 | 5 |
| 3,5-F₂ | O | H | Cl | O | CH₃ | 2-Cl | 4 | 5 |
| 3,5-F₂ | O | H | Cl | O | C₂H₅ | 2-Cl | 4 | 5 |
| 3,4-Cl₂ | O | H | Cl | O | CH₃ | 2-Cl | 4 | 5 |
| 3-F | O | H | Cl | O | H | 2-Cl | 4 | 5 |
| 3,4-F₂ | O | H | Cl | O | (iso)C₃H₇ | 2-Cl | 4 | 5 |

Examples of the insect pests against which the pyridine derivatives (I) of the invention exhibit controlling effects are as shown below.

Hemiptera

Planthoppers such as brown planthopper (*Nilaparvata lugens*), white-backed rice planthopper (*Sogatella furcifera*) and small brown planthopper (*Laodelphax striatellus*); leafhoppers such as green rice leafhopper (*Nephotettix cinticeps*), *Nephotettix virescense, Nephotettix nigropictus*, zig-zag rice leafhopper (*Recilia dorsalis*), tea green leafhopper (*Empoasca onukii*) and grape leafhopper (*Arboridia apicalis*); aphids such as cotton aphid (*Aphis gossypii*) and green peach aphid (*Myzus persicae*); bugs; whiteflies (Aleyrodiae) such as sweet potato whitefly (*Bemisia tabaci*) and greenhouse whitefly (*Trialeurodes vaporariorum*); scales; mealy bugs; lace bugs (Tingidae); psyllids (Psyllidae), etc.

Lepidoptera

Pyralid moths (Pyralidae) such as rice stem borer (*Chilo suppressalis*), rice leafroller (*Cnaphalocrocis medinalis*) and Indian meal moth (*Plodia interpunctella*); Noctuidae such as tobacco curworm (*Spodoptera litura*), rice armyworm (*Pseudaletia separate*), cabbage armyworm (*Mamestra brassicae*) and beet semi-looper (*Autographa nigrisigna*); *Agrothis* spp. such as turnip cutworm (*Agrothis segetum*) and black cutworm (*Agrothis ipsilon*); *Heliothis spp.*; Pieridae such as common cabbageworm (*Pieris rapae crucivora*); tortricid moths (Tortricidae) such as *Adoxophyes* spp. and *Grapholita* spp.; Carposinidae such as lyonetiid moths (Lyonetiidae), leafblotch miners (Gracillariidae), gelechiid moths (Gelechiidae) and tussock moths (Lymantriidae); diamondback moth (*Plutella xylostella*), clothes moths (Tineidae), casemaking clothes moth (*Tinea translucens*) and webbing clothes moth (*Tineola bisselliella*), etc.

Diptera

Mosquitos (Calicidae) such as common mosquito (*Culex pipiens pallens*) and *Culex tritaeniorhynchus*; *Aedes* spp. such as *Aedes aegypti* and *Aedes albopictus*; *Anopheles* spp. such as *Anopheles sinensis*; midges (Chironomidae); Muscidae such as housefly (*musca domestica*) and false stablefly (*Muscina stabulans*); Calliphoridae; Sarcophagidae; lesser housefly (*Fannia canicularis*); anthomyiid flies (Anthomyiidae) such as seedcorn maggot (*Delia platura*) and onion maggot (*Delia antique*); fruit flies (Tephritidae); shore flies (*Ephydridae*); small fruit flies (Drosophilidae); moth flies (Psychodidae); black flies (Simuliidae); Tabanidae; stable flies (Stomoxyidae); etc.

Coleoptera

Leaf beetles (Chrysomelidae) such as cucurbit beetle (*Aulacophora femoralis*), striped flea beetles (*Phyllotrata striolata*), western corn rootworm (*Diabrotica virgifora*) and southern corn root worm (*Diabrotica undecimpunctata*); scarabs (Scarabaeidae) such as cupreous chafer (*Anomala cuprea*) and soybeen beetle (*Anomala rufocuprea*); weevils (Cureulionidae) such as maize weevil (*Sitophilus zeamais*), rice water weevil (*Lissorhoptrus oryzophilus*) and adzuki bean weevil (*Callosobruchys chineneis*), etc.; darkling beetles (Tenebrionidae) such as yellow mealworm (*Tenebrio moliter*) and red fluor beetles (*Tribolium castaneum*); Anobiidae; Coccinellidae such as twenty-eight-spotted ladybirds (*Epilachna vigintioctopunctata*); powderpost beetles (Lyctidae); false powderpost beetles (Bostrychidae); Cerambysidae, etc.

Dictyoptera

Blattellidae such as German cockroach (*Blattella germanica*); Blattidae such as smokybrown cockroach (*Periplaneta fuliginosa*), American cockroach (*Periplaneta americana*), brown cockroach (*Periplaneta brunnea*) and oriental cockroach (*Blatta orientalis*), etc.

Thysanoptera

Thrips such as *Thrips palmi*, yellow tea thrips (*Scirtothrips dorsalis*) and flower thrips (*Thrips hawaiiensis*), etc.

Hymenoptera

Ants (Formicidae); sawflies (Tenthredinidae) such as cabbage sawfly (*Athalia rosae ruficornis*), etc.

Orthoptera

Mole crickets (Gryllotalpidae); grasshoppers (Acrididae), etc.

Aphaniptera

*Purex irritans*, etc.

Anoplura

*Pediculus hunanus capitis*, *Phthirus pubis*, etc.

Isoptera

*Reticulitermes speratus*, Formosan subterrauean terminte (*Coptotermes formosanus*), etc.

Among the insect pests as above exemplified, the pyridine derivatives (I) are particularly effective in controlling those belonging to Hemiptera and also exhibit a remarkable controllable effect on planthoppers and leaf-hoppers in a field of rice plant.

The pyridine derivatives (I) may be used alone as insecticides or in mixtures with other insecticides and/or acaricides to enhance or expand their insecticidal or pesticidal use.

Examples of the other insecticides and acaricides are carbamate derivatives such as BPMC (2-sec-butylphenyl methylcarbamate), benfuracarb (ethyl N-[2,3-dihydro-2,2-dimethylbenzofuran-7-yloxycarbonyl(methyl-)aminothio]-N-isopropyl-beta-alaninate), propoxur (2-isopropoxyphenyl N-methylcarbamate), carbosulfan (2,3-dihydro-2,2-dimethyl-7-benzo[6]furanyl N-methylcarbamate), carbaryl (1-naphtyl-N-methylcarbamate), methomyl (S-methyl-N-[(methylcarbamoyl)-oxy]thioacetimidate), ethiofencarb (2-(ethylthiomethyl)-phenyl methylcarbamate), aldicarb (2-methyl-2-(methylthio)propionaldehyde O-methylcarbamoyloxime) and oxamyl (N,N-dimethyl-2-methylcarbamoyloxyimino-2-(methylthio)acetamide); pyrethroids such as ethofenprop (2-(4-ethoxyphenyl)-2-methylpropyl-3-phenoxybenzyl ether), fenvalerate ((RS)alpha-cyano-3-phenoxybenzyl (RS)-2-(4-chlropheny)-3-methylbutyrate), esfenvalerate ((S)-alpha-cyano-3-phenoxybenzyl (S)-2-(4-chlorophenyl)-3-methylbutyrate), fenpropathrin ((RS)-alpha-cyano-3-pnenoxybenzyl 2,2,3,3-tetramethylcyclopropanecarboxylate), cypermethrin ((RS)-alpha-cyano-3-phenoxybenzyl (1RS,3RS)-(1RS,3RS)-3-(2,2-dichlorovinyl)2,2-dimethylcyclopropanecarboxylate), permethrin (3-phenoxybenzyl (1RS,3RS)-(1RS,3RS)-3-(2,2-dichlorovinyl)-2,2-dimethylcyclopropanecarboxylate), cyhalothrin ((R,S)-alphacyano-3-phenoxybenzyl (Z)-(1RS,3RS)-3-(2-chloro-3,3,3-trifluoropropenyl)-2,2-dimethylcyclopropanecarboxylate), deltamethrin ((S)-alpha-cyano-m-phenoxybenzyl (1R,3R)3-(2,2-dibromovinyl)-2-dimethylcyclopropanecarboxylate) and cycloprothrin ((RS)-alpha-cyano-3-phenoxybenzyl (RS)-2,2-dichloro-1-(4-ethoxyphenyl)cyclopropanecarboxylate); thiadiazine derivatives such as buprofezin (2-tert-butylimino-3-isopropyl-5-phenyl-1,3,5-triadiazin-4-one); nitroimidazolidine derivatives such as imidacloprid (1-(6-chloro-3-pyridylmethyl)-N-nitroimidazolidine-2-ylideneamine); nereistoxin derivatives such as cartap (S,S'-(2-dimethylaminotrimethylene)bis(-thiocarbamate)), thiocyclam (N,N-dimethyl- 1,2,3-trithian-5-ylamine) and bensultap (S,S'-2-dimethylaminotrimethylene di(benzenethiosulphonate)); halogenated hydrocarbons such as endosulfan (6,7,8,9,10,10-hexachloro-1,5,5a,6,9,9a-hexahydro-6,9-methano-2,4,3-benzodioxathiepin-3-oxide) and gamma-BHC (1,2,3,4,5,6-hexachlorocyclohexane); benzoylphenylurea derivatives such as chlorfluazuron (1-[3,5-dichloro-4-(3-chloro-5-trifluoromethylpyridin-2-yloxy)phenyl]-3-(2,6-difluorobenzoy teflubenzuron (1-(3,5-dichloro-2,4-difluorophenyl)-3-(2,6-difluorobenzoyl)urea) and flufenoxuron (1-[4-(2-chloro-4-trifluoromethylphenoxy)-2-fluorophenyl]-3-(2,6-difluorobenzoyl)urea); formamidine derivatives such as amitraz (N,N'-[(methylimino)-dimethylidyne]-di-2,4-xylidine) and chlordimeform (N'-(4-chloro-2-methylphenyl)-N,N-dimethylmethanimidamide), etc.

On the practical use of the pyridine derivatives (I) as insecticides, they may be employed as such but are normally mixed with appropriate additivies such as solid carriers, liquid carriers, gaseous carriers, feed, etc. to formulate their compositions. When desired or necessary, surfactants and other adjuvants may be further incorporated therein. The compositions may be prepared into any conventional forms such as oil sprays, emulsifiable concentrates, wettable powders, flowable concentrates (e.g. water-based suspension formulations, water-based emulsion formulations), granules, dusts, aerosals, heating smoking formulations (e.g. self-burning-type smoking formulations, chemical reaction-type smoking formulations, porous ceramic plate-type smoking formulations), ULV formulations, poison baits, etc.

The composition of the invention contains generally the pyridine derivative(s) (I) as the active ingredient in an amount of from about 0.001% to 95% by weight based on the composition.

Examples of the solid carrier usable for making the composition are fine powders or granules of clays (e.g. kaolin clay, diatomaceous earth, synthetic hydrated silica, bentonite, Fubasami clay terra alba), talc, ceramics, other inorganic minerals (e.g. sericite, quartz, sulfur, activated carbon, calcium carbonate, hydrated silica), chemical fertilizers (e.g. ammonium sulfate, ammonium phosphate, ammonium nitrate, urea, ammonium chloride), etc. Examples of the liquid carrier include water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. hexane, cyclohexane, kerosene, gas oil), esters (e.g. ethyl acetate, butyl acetate, etc.), nitriles (e.g. acetonitriles, isobutyronitrile), ethers (e.g. diisopropyl ether, dioxane), acid amides (e.g. N,N-dimethylformamide, N,N-dimethylacetamide), halogenated hydrocarbons (e.g. dichloromethane, trichloroethane, carbon tetrachloride), dimethylsulfoxide, vegetable oils (e.g. soybean oil, cotton seed oil), etc. Examples of the gaseous carrier, i.e. a propellant, include freon gas, butane gas, LPG (liquefied petroleum gas), dimethyl ether, carbon dioxide, etc.

Examples of the surfactant are alkylsulfates, alkylsulfonates, alkylarylsulfonates, alkyl aryl ethers and polyoxyethylene derivatives thereof, polyethylene glycol ethers, polyvalent alcohol esters, sugar alcohol derivatives, etc. Examples of the adjuvants such as binders and dispersing agents are casein, gelatin, polysaccharides (e.g. starch powders, gum arabic, cellulose derivatives, alginic acid), lignin derivatives, bentonite, sugars, synthetic water-soluble high molecular weight substances (e.g. polyacrylic alcohol, polyvinylpyrrolidone, polyacrylic acid), etc. Examples of the stabilizer include PAP (acidic isopropyl phosphate), BHT (2,6-di-tert-butyl-4-methyl-phenol), BHA (mixture of 2-tert-butyl-4-methoxyphenol and 3-tert-butyl-4-methoxyphenol), vegetable oils, mineral oils, surfactants, fatty acids or esters thereof, etc.

The base material for self-burning-type smoking formulations may include, for example, burning heat-generating agents such as nitrates, nitrites, guanidine salts, potassium chlorate, nitrocellulose, ethyl cellulose and wood powders, pyrolysis-promoting agents such as alkali metal salts, alkaline earth metal salts, dichromates and chromates, oxygen-supplying agents such as potassium nitrate, burning-supporting agents such as melamine and wheat starch, extenders such as diatomaceous earth, binders such as synthetic pastes, etc. The base material for chemical reation-type smoking formulations can include, for example, heat-generating agents such as alkali metal sulfides, alkali metal polysulfides, alkali metal hydrosulfides, hydrated salts of alkali metals and calcium oxide, catalyzing agents such as carbonaceous substances, iron carbide and activated clay, organic foaming agents such as azodicarbonamide, benzenesulfonyl hydrazides, dinitrosopentamethylenetetramine, polystyrene and polyurethane, fillers such as natural fiber pieces and synthetic fiber pieces, etc. The base material for poison baits may contain feed components such as crop powders, essential vegetable oil, sugars and crystalline cellulose, antioxidants such as dibutylhydroxyrtolune and nordihydroguaiaretic acid, preservatives such as dehydroacetic acid, feeding error preventing agents such as red paper powders, incentive flavors such as cheese flavor and onion flavor, etc.

Flowable concentrates (water-based suspension or emulsion formulations) are generally obtained by dispersing about 1 to 75 parts by weight of the pyridine derivative (I) as the active ingredient finely and uniformly into water containing about 0.5 to 15 parts by weight of a dipersing agent, about 0.1 to 10 parts by weight of a suspending agent (e.g. protective colloids, compounds giving a thixotropic property) and optionally about 0 to 10 parts by weight of an auxiliary agent(s) such as a defoaming agent, an anti-corrosive agent, a stabilizing agent, a spreading agents, penetration auxiliaries, antifreezing agent, an anti-bacterial agent, an antimolding agent and the like. The use of an oil, into which the active ingredient is hardly soluble, in place of water affords oil-based suspension formulations. Examples of the protective colloids as above mentioned are gelatin, casein, gums, cellulose, ethers, polyvinyl alcohol, etc. Examples of the compounds giving a thixotropic property are bentonite, aluminum magnesium silicate, xanthane gum, polyacrylic acid, etc.

The composition of the invention thus obtained may be used as such or after diluting with water. It may be also used in a mixture with any other active component or composition chosen from insecticides, nematocides, acaricides, fungicides, bacteriocides, herbicides, plant growth regulators, synergistic agents, fertilizers, soil conditioners, animal feed, etc. Alternatively, the composition of the invention may be applied separately but simultaneously with said other active component or composition.

For the purpose of controlling insect pests in the agricultural field, the pyridine derivative (I) according to the present invention may be applied to the insect pests or the locus where the insect pests propagate generally in an amount of about 0.001 g to 500 g, and preferably about 0.1 g to 500 g per 10 ares. when the pyridine derivative (I) is applied in a form of emulsifiable concentrate, wettable powder, flowable concentrate or the like after dilution with water, its concentration may be from about 0.0001 to 1000 ppm. Granules, dusts, etc. may be used as such, i.e. without water dilution. When the pyridine derivative (I) is used for household or public hygiene, it may be used in the form of emulsifiable concentrate, wettable powder, flowable concentrate or the like with water dilution, etc. In this case, the concentration of the active ingredient may be from about 0.0001 to 10,000 ppm. In case of oils, aerosol, fumigants, ULV formulations, poison baits, etc., they may be applied as such. However, the doses and concentrations may vary within broad ranges depending upon the composition, the application time, the place applied, the application method, the kind of insect pests, the condition of damage, etc. and may be increased or decreased, irrespective of the general ranges set forth above.

Practical and presently preferred embodiments of the invention will be hereinafter explained in more detail referring to Production Examples, Formulation Examples and Test Examples. These examples, however, should not be construed to be limitative.

In the following Production Examples, % is by weight unless otherwise indicated.

PRODUCTION EXAMPLE 1

Production of Compound No. 1

To a solution of 0.09 g of sodium hydride (60% oil dispersion) in 10 ml of N,N-dimethylformamide, there was added dropwise a solution of 0.45 g of 2-chloro-4-phenoxyphenol in 3 ml of N,N-dimethylformamide with stirring and ice-cooling. After 30 minutes, a solution of 0.34 g of 2-chloro-5-chloromethylpyridine in 5 ml of N,N-dimethylformamide was added thereto at room temperature, followed by stirring at the same temperature for 10 hours. The reaction mixture was poured into ice-water and extracted twice with 100 ml of ethyl acetate. The extracts were combined together, washed with water, dried over anhydrous magnesium sulfate and concentrated under reduced pressure. The residue was subjected to silica gel chromatography to give 0.50 g of 2-chloro-5-(2-chloro-4-phenoxyphenoxy)-methylpyridine. Yield, 71%. n22 1.6173 Yield, 71%. $n_D^{22}$: 1.6173

PRODUCTION EXAMPLE 2

Production of Compound No. 33

To a solution 0.07 g of sodium hydride (60% oil dispersion) in 10 ml of N,N-dimethylformamide, there was added dropwise a solution of 0.50 g of 2-chloro-4-(3-trifluoromethylphenoxy)phenol in 3 ml of N,N-dimethylformamide with stirring and ice-cooling. After 30 minutes, a solution of 0.28 g of 2-chloro-5-chloromethylpyridine in 5 ml of N,N-dimethylformamide was added thereto at room temperature, followed by stirring at the same temperature for 10 hours. The reaction mixture was poured into ice-water and extracted twice with 100 ml of ethyl acetate. The extracts were combined together, dried over anhydrous magnesium sulfate and concentrated under reduced pressure. The residue was subjected to silica gel chromatography to give 2-chloro-5[[2-chloro-4-(3-trifluoromethylphenoxy)phenoxy]methylpyridine.

PRODUCTION EXAMPLE 3

Production of Compound No. 34

To a solution of 0.07 g of sodium hydride (60% oil dispersion) in 10 ml of N,N-dimethylformamide, there is added dropwise a solution of 0.50 g of 2-chloro-4-(3-bromophenoxy)phenol in 3 ml of N,N-dimethylformamide with stirring and ice-cooling. After 30 minutes, a solution of 0.27 g of 2-chloro-5-chloromethylpyridine in 5 ml of N,N-dimethylformamide is added thereto at room temperature, followed by stirring at the same temperature for 10 hours. The reaction mixture is poured into ice-water and extracted twice with 100 ml of ethyl acetate. The extracts are combined together, washed with water, dried over anhydrous magnesium sulfate and concentrated under reduced pressure. The residue is subjected to silica gel chromatography to give 2-chloro-5-[4-(3-bromophenoxy)-2-chlorophenoxy]methylpyridine.

PRODUCTION EXAMPLE 4

Production of Compound No. 17

A mixture of 0.82 g of 2-chloro-5-phenoxyphenol, 0.54 g of 2-methyl-5-hydroxymethylpyridine, 1.01 g of triphenylphosphine, 0.65 g of diethyl azadicarboxylate and 90 ml of tetrahydrofuran was stirred at room temperature. After 48 hours, the reaction mixture was concentrated, and 50 ml of diethyl ether were added thereto. The precipitate was removed by filtration, and the filtrate was concentrated. The residue was subjected to silica gel chromatography to give 0.66. g of 2-methyl-5-(2-chloro-5-phenoxyphenoxy)methylpyridine. Yield, 51%. m.p., 64.9° C.

PRODUCTION EXAMPLE 5

Production of Compound No. 35

A mixture of 0.80 g of 2-chloro-5-phenoxyphenol, 0.57 g of 2-chloro-5-(1-hydroxyethyl)pyridine, 0.95 g of triphenylphosphine, 0.63 g of diethyl azadicarboxylate and 100 ml of tetrahydrofuran is stirred at room temperature. After 48 hours, the reaction mixture is concentrated, and 50 ml of diethyl ether are added thereto. The precipitate is removed by filtration, and the filtrate is concentrated. The residue is subjected to silica gel chromatography to give 2-chloro-5-[1-(2-chloro-4-phenoxyphenoxy)ethyl]pyridine.

Some examples of the pyridine derivatives (I) as produced in the same manner as above are shown in Table 2.

TABLE 2

| Compound No. | Chemical structure | Physical constant |
| --- | --- | --- |
| 1 | ⟨phenyl⟩-O-⟨Cl-phenyl⟩-O-CH(H)-⟨pyridyl-Cl⟩ | $n_D^{22}$ 1.6173 |

TABLE 2-continued

| Compound No. | Chemical structure | Physical constant |
|---|---|---|
| 2 | 4-phenoxy-2-fluoro-phenyl-O-CH(H)-(2-chloropyridin-5-yl) | $n_D^{25}$ 1.5843 |
| 3 | 4-phenoxy-2-bromo-phenyl-O-CH(H)-(2-chloropyridin-5-yl) | m.p. 109.4° C. |
| 4 | 4-phenoxy-2-methyl-phenyl-O-CH(H)-(2-chloropyridin-5-yl) | m.p. 65.6° C. |
| 5 | 3-fluorophenoxy-2-chloro-phenyl-O-CH(H)-(2-chloropyridin-5-yl) | m.p. 83.5° C. |
| 6 | 3,5-difluorophenoxy-2-chloro-phenyl-O-CH(H)-(2-chloropyridin-5-yl) | m.p. 93.9° C. |
| 7 | 3,4-dichlorophenoxy-2-chloro-phenyl-O-CH(H)-(2-chloropyridin-5-yl) | $n_D^{22}$ 1.6142 |
| 8 | benzyl-2-chloro-phenyl-O-CH(H)-(2-chloropyridin-5-yl) | m.p. 98.4° C. |
| 9 | 2,4-difluorophenoxy-2-chloro-phenyl-O-CH(H)-(2-chloropyridin-5-yl) | m.p. 79.3° C. |
| 10 | phenoxy-2-chloro-phenyl-O-CH(H)-(6-methylpyridin-3-yl) | $n_D^{22}$ 1.6090 |

TABLE 2-continued

| Compound No. | Chemical structure | Physical constant |
|---|---|---|
| 11 | 3,5-difluorophenyl–O–(2-chloro-phenyl)–O–CH(H)–(6-methylpyridin-3-yl) | m.p. 77.2° C. |
| 12 | 3-methylphenyl–O–(2-chloro-phenyl)–O–CH(H)–(6-methylpyridin-3-yl) | m.p. 49.6° C. |
| 13 | 3,4-dichlorophenyl–O–(2-chloro-phenyl)–O–CH(H)–(6-methylpyridin-3-yl) | $n_D^{23}$ 1.6083 |
| 14 | phenyl–CH$_2$–(2-chloro-phenyl)–O–CH(H)–(6-methylpyridin-3-yl) | $n_D^{23}$ 1.5939 |
| 15 | phenyl–O–(2-chloro-phenyl)–O–CH(H)–(2,6-dichloropyridin-4-yl) | $n_D^{22}$ 1.6157 |
| 16 | phenyl–O–(4-chloro-phenyl)–O–CH(H)–(6-chloropyridin-3-yl) | m.p. 88.1° C. |
| 17 | phenyl–O–(4-chloro-phenyl)–O–CH(H)–(6-methylpyridin-3-yl) | m.p. 64.9° C. |
| 18 | 3,4-dimethylphenyl–O–(2-chloro-phenyl)–O–CH(H)–(6-chloropyridin-3-yl) | m.p. 89.8° C. |
| 19 | 3-chlorophenyl–O–(4-chloro-phenyl)–O–CH(H)–(6-chloropyridin-3-yl) | $n_D^{24}$ 1.6208 |

TABLE 2-continued

| Compound No. | Chemical structure | Physical constant |
|---|---|---|
| 20 | 3-F-C6H4-CH2-(3-Cl-C6H3)-O-CH(H)-(2-Cl-pyridin-5-yl) | m.p. 93.7° C. |
| 21 | (3,5-F2-C6H3)-O-(2-Cl,5-Cl-C6H2)-O-CH(H)-(2-Cl-pyridin-5-yl) | m.p. 84.2° C. |
| 22 | (3,5-F2-C6H3)-O-(4-Cl-C6H3)-O-CH(H)-(2-Cl-pyridin-5-yl) | m.p. 95.5° C. |
| 23 | 3-Cl-C6H4-CH2-(3-Cl-C6H3)-O-CH(H)-(2-Cl-pyridin-5-yl) | m.p. 79.9° C. |
| 24 | 4-F-C6H4-O-(3-Cl-C6H3)-O-CH(H)-(2-Cl-pyridin-5-yl) | m.p. 73.6° C. |
| 25 | 4-CH3-C6H4-O-(3-Cl-C6H3)-O-CH(H)-(2-Cl-pyridin-5-yl) | m.p. 75.4° C. |
| 26 | (2,4-F2-C6H3)-O-(2,6-Cl2-C6H2)-O-CH(H)-(2-Cl-pyridin-5-yl) | m.p. 79.3° C. |
| 27 | (3,5-F2-C6H3)-CH2-(3-Cl-C6H3)-O-CH(H)-(2-Cl-pyridin-5-yl) | m.p. 110.6° C. |
| 28 | (2,4-Cl2-C6H3)-O-(3-Cl-C6H3)-O-CH(H)-(2-Cl-pyridin-5-yl) | m.p. 94.2° C. |

TABLE 2-continued

| Compound No. | Chemical structure | Physical constant |
|---|---|---|
| 29 | 3,4-Cl$_2$-C$_6$H$_3$-CH$_2$-(3-Cl-C$_6$H$_3$)-O-CH(H)-(6-Cl-pyridin-3-yl) | m.p. 108.1° C. |
| 30 | 3,5-Cl$_2$-C$_6$H$_3$-O-(3-Cl-C$_6$H$_3$)-O-CH(H)-(6-Cl-pyridin-3-yl) | $n_D^{22}$ 1.6201 |
| 31 | 4-Cl-C$_6$H$_4$-O-(3-Cl-C$_6$H$_3$)-O-CH(H)-(6-Cl-pyridin-3-yl) | m.p. 103.8° C. |
| 32 | 4-Cl-C$_6$H$_4$-O-(3-Cl-C$_6$H$_3$)-O-CH(H)-(6-CH$_3$-pyridin-3-yl) | m.p. 76.1° C. |
| 33 | 3-F$_3$C-C$_6$H$_4$-O-(3-Cl-C$_6$H$_3$)-O-CH(H)-(6-Cl-pyridin-3-yl) | |
| 34 | 3-Br-C$_6$H$_4$-O-(3-Cl-C$_6$H$_3$)-O-CH(H)-(6-Cl-pyridin-3-yl) | |
| 35 | C$_6$H$_5$-O-(3-Cl-C$_6$H$_3$)-O-CH(CH$_3$)-(6-Cl-pyridin-3-yl) | |
| 36 | 3,4-Cl$_2$-C$_6$H$_3$-O-(2-Cl-C$_6$H$_3$)-O-CH(H)-(6-Cl-pyridin-3-yl) | m.p. 105.2° C. |
| 37 | 3,5-Cl$_2$-C$_6$H$_3$-O-(3-Cl-C$_6$H$_3$)-O-CH(H)-(6-CH$_3$-pyridin-3-yl) | $n_D^{23}$ 1.6352 |

TABLE 2-continued

| Compound No. | Chemical structure | Physical constant |
|---|---|---|
| 38 | 4-Cl-C6H4-O-(2-Cl-C6H3)-O-CH(H)-(pyridin-3-yl with 6-Cl) | m.p. 98.5° C. |
| 39 | 2,4-F2-C6H3-O-(2-Cl-C6H3)-O-CH(H)-(pyridin-3-yl with 6-CH3) | m.p. 50.8° C. |
| 40 | 3-Cl-C6H4-O-(2-Cl-C6H3)-O-CH(H)-(pyridin-3-yl with 6-CH3) | m.p. 69.5° C. |

PRODUCTION EXAMPLE 6

Production of Compound No. 42 as an intermediate

To a solution of 5.0 g p-(3,5-difluorophenoxy)phenol in 50 mg of carbon tetrachloride, there were added dropwise 2.45 g of tert-butylhypochlorous acid with stirring and ice-cooling, and stirring was continued at room temperature of 5 hours. The reaction mixture was concentrated and extracted with 200 ml of ethyl acetate. The extract was washed with 5% aqueous solution of sodium bicarbonate, dried over anhydrous magnesium sulfate and concentrated under reduced pressure. The residue was subjected to silica gel chromatography to give 5.31 g of 2-chloro-4-(3,5-difluorophenoxy)phenol. Yield, 92%. $n_D^{25}$: 1.5639

The compounds useful as the intermediates, which are produced in the same manner as above, are shown in Table 3.

TABLE 3

| Compound No. | Chemical structure | Physical constant |
|---|---|---|
| 41 | 3-F-C6H4-O-(2-Cl-C6H3)-OH | $n_D^{25}$ 1.5846 |
| 42 | 3,5-F2-C6H3-O-(2-Cl-C6H3)-OH | $n_D^{25}$ 1.5639 |
| 43 | 3,4-Cl2-C6H3-O-(2-Cl-C6H3)-OH | $n_D^{25}$ 1.5960 |
| 44 | 3,4-F2-C6H3-O-(2-Cl-C6H3)-OH | $n_D^{25}$ 1.5960 |
| 45 | 3-CH3-C6H4-O-(2-Cl-C6H3)-OH | $n_D^{25}$ 1.5886 |
| 46 | 3,4-(CH3)2-C6H3-O-(2-Cl-C6H3)-OH | $n_D^{25}$ 1.5934 |
| 47 | 3-Cl-C6H4-O-(2-Cl-C6H3)-OH | $n_D^{21.5}$ 1.6098 |
| 48 | 3,5-F2-C6H3-O-(2-Cl-C6H3)-OH | $n_D^{21.4}$ 1.5670 |
| 49 | 4-F-C6H4-O-(2-Cl-C6H3)-OH | $n_D^{23}$ 1.5170 |

TABLE 3-continued

| Compound No. | Chemical structure | Physical constant |
|---|---|---|
| 50 | 3-Cl-C6H4-O-C6H3(2-Cl)(OH) | $n_D^{25}$ 1.5930 |
| 51 | 4-CH3-C6H4-O-C6H3(2-Cl)(OH) | $n_D^{23}$ 1.6109 |
| 52 | 3,5-Cl2-C6H3-O-C6H3(2-Cl)(OH) | $n_D^{24}$ 1.5824 |
| 53 | 3-CF3-C6H4-O-C6H3(2-Cl)(OH) | |
| 54 | 3-Br-C6H4-O-C6H3(2-Cl)(OH) | |
| 55 | 3,5-F2-C6H3-O-C6H2(2-Cl)(5-Cl)(OH) | $n_D^{23}$ 1.5650 |
| 56 | 3,5-F2-C6H3-O-C6H2(2-Cl)(5-Cl)(OH) | m.p. 76.8° C. |
| 57 | 3-Cl-C6H4-O-C6H2(2-Cl)(5-Cl)(OH) | m.p. 80.6° C. |

In Formulation Examples as set forth below, parts and % are all by weight. The compound numbers correspond to those as shown in Table 2.

FORMULATION EXAMPLE 1

Emulsifiable concentrate

To a solution of 10 parts of each of Compounds Nos. 1 to 40 in 35 parts of xylene and 35 parts of dimethylformamide, 14 parts of polyoxyethylene styrylphenyl ether and 6 parts of calcium dodecylbenzenesulfonate are added, and the resultant mixture is thoroughly mixed while stirring to give an emulsifiable concentrate containing the active ingredient in 10%.

FORMULATION EXAMPLE 2

Wettable Powder

Twenty parts of each of Compounds Nos. 1 to 40 are added to a mixture of 4 parts of sodium laurylsulfate, 2 parts of calcium ligninsulfonate, 20 parts of fine powders of synthetic hydrated silica and 54 parts of diatomaceous earth, and the resultant mixture is stirred in a mixer to give a wettable powder containing the active ingredient in 20%.

FORMULATION EXAMPLE 3

Granules

Five parts of sodium dodecylbenzenesulfonate, 30 parts of bentonite and 60 parts of clay are added to 5 parts of each of Compound Nos. 1, 2, 7, 10, 13 to 15, 19, 30 and 37, and the resultant mixture is pulverized and kneaded with a suitable amount of water. The mixture is granulated in a granulator and air-dried to give granules containing the active ingredient in 5%.

FORMULATION EXAMPLE 4

Granules

Five parts of fine powders of synthetic hydrated silica, 5 parts of sodium dodecylbenzenesulfonate, 30 parts of bentonite and 55 parts of clay are added to 5 parts of each of Compound Nos. 3 to 6, 8, 9, 11, 12, 16 to 18, 20 to 29, 31, 32, 36, 38 to 40, and the resultant mixture is pulverized and kneaded with a suitable amount of water. The mixture is granulated in a granulator and air-dried to give granules containing the active ingredient in 5%.

FORMULATION EXAMPLE 5

Dusts

To a mixture of 1 part of fine powders of synthetic hydrated silica, 1 part of an aggregating agent ("Driless B" manufactured by Sankyo Co., Ltd.) and 7.7 parts of clay, 0.3 part of each of Compound Nos. 1, 2, 7, 10, 13 to 15, 19, 30 and 37 is added, and the resultant mixture is well pestled in a mortar and further stirred in a mixer. To the thus obtained mixture, there are added 90 parts of cut clay, followed by mixing to give dusts containing the active ingredient in 0.3%.

FORMULATION EXAMPLE 6

Dusts

A mixture of 0.3 part of each of Compound Nos. 3 to 6, 8, 9, 11, 12, 16 to 18, 20 to 29, 31, 32, 36 and 38 to 40 and 0.03 part of fine powders of synthetic hydrated silica is stirred well in a mixer and pulverized by the aid of a centrifugal pulverizer. To the resultant mixture, 0.97 part of fine powders of synthetic hydrated silica, 1 part of "Driless B" and 7.7 parts of clay are added, and the resulting mixture is pestled in a mortar and stirred in a mixer. Ninety parts of cut clay are added thereto, and further mixing is effected in a sack to give dusts containing the active ingredient in 0.3%.

FORMULATION EXAMPLE 7

Dusts

A mixture of 0.3 part of each of Compound Nos. 1, 2, 7, 10, 13 to 15, 19, 30 and 37, 2 parts of BPMC (O-secbuthylphenyl N-methylcarbamate) as a carbamate insecticide, 3 parts of fine powders of synthetic hydrated silica, 1 part of "Driless B" and 3.7 parts of clay are pestled in a mortar and stirred in a mixer. Then, 90 parts of cut clay are added thereto, and the resultant mixture is further mixed in a sack to give dusts.

FORMULATION EXAMPLE 8

Dusts

A mixture of 0.3 part of each of Compound Nos. 3 to 6, 8, 9, 11, 12, 16 to 18, 20 to 29, 31, 32, 36 and 38 to 40 and 0.03 part of fine powders of synthetic hydrated silica is stirred in a mixer and pulverized by a centrifugal pulverizer. After addition of 2 parts of BPMC (O-sec-butylphenyl N-methylcarbamate), 2.97 parts of fine powders of synthetic hydrated silica, 1 part of "Driless B" and 3.7 parts of clay thereto, the resultant mixture is pestled in a mortar and stirred in a mixer. Then, 90 parts of cut clay are added thereto, and the resultant mixture is further mixed in a sack to give dusts.

FORMULATION EXAMPLE 9

Dusts

To a solution of 1 part of each of Compound Nos. 1 to 40 in an appropriate amount of acetone, 5 parts of fine powders of synthetic hydrated silica, 0.3 part of PAP (acidic isopropyl phosphate) and 93.7 parts of clay are added, and the resultant mixture is stirred in a mixer, followed by evaporation of acetone to give dusts containing the active ingredient in 1%.

FORMULATION EXAMPLE 10

Dusts

To 40 parts of an aqueous solution containing 2 parts of polyvinyl alcohol, 10 parts of each of Compound Nos. 1, 2, 7, 10, 13 to 15, 19, 30 and 37 are added, and the resultant mixture is stirred in a mixer. To the thus obtained dispersion, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 10%.

FORMULATION EXAMPLE 11

Flowable concentrate

To 28.5 parts of an aqueous solution containing 2 parts of polyvinyl alcohol, 20 parts of each of Compound Nos. 3 to 6, 8, 9, 11, 12, 16 to 18, 20 to 29, 31, 32, 36 and 38 to 40 and 1.5 parts of sorbitan trioleate are added, and the resultant mixture is finely pulverized by the aid a sand grinder to give particles of less than 3 microns in average particle size. To the resultant mixture, 40 parts of an aqueous solution containing 0.05 part of xanthane gum and 0.1 part of aluminum magnesium silicate are added, followed by addition of 10 parts of propylene glycol. The mixture is gently stirred to give a flowable concentrate containing the active ingredient in 20%.

FORMULATION EXAMPLE 12

Oil spray

Into a mixture of 5 parts of xylene and 5 parts of trichloroethane, 0.1 part of each of Compound Nos. 1 to 40 is dissolved, and the resultant solution is mixed with 89.9 parts of deodorized kerosene to give an oil spray containing the active ingredient in 0.1%.

FORMULATION EXAMPLE 13

Oil-based aerosol

A solution of 0.1 part of each of Compound Nos. 1 to 40, 0.2 part of tetramethrin (2,2-dimethl-3-(2-methyl-1-propenyl)cyclopropanecarboxylic acid (1,2,3,4,5,7-hexahydro-1,3-dioxo-2H-isoindol-2-yl)methyl ester) and 0.1 part of d-phenothrin (2,2-dimethyl-3-(2-methyl-1-propenyl)cyclopropanecarboxylic acid (3-phenoxyphenyl)methyl ester) in a mixture of 10 parts of trichloroethane and 59.6 parts of deodorized kerosene is filled in an aerosol container. After provision of a valve, 30 parts of a propellant (liquefied petroleum gas) is filled through the valve under reduced pressure to give an oil-based aerosol.

FORMULATION EXAMPLE 14

Water-based aerosol

A solution of 0.2 part of each of Compound Nos. 1 to 40, 0.2 part of d-allethrin ((2,2-dimethyl-3-(2-methyl-1-propenyl)cyclopropanecarboxylic acid 2-methyl-1-propenyl)-2-cyclopenten-2-yl ester), 0.2 part of d-phenothrin, 5 parts of xylene, 3.4 parts of deodorized kerosen and 1 part of an emulsifier ("ATMOS 300" ®, Atlas Chemical Co., Ltd.) in 50 parts of distilled water is filled in an aerosol container. After provision of a valve, 40 parts of a propellant (liquefied petroleum gas) is filled through the valve under reduced pressure to give a water-based aerosol.

FORMULATION EXAMPLE 15

Fumigant

Each of Compound Nos. 1 to 40 (100 mg) is dissolved in an appropriate amount of acetone, and the resultant solution is impregnated with a porous ceramic plate (4.0×4.0×1.2 cm) to give a fumigant.

The following Test Examples show some of test results which support the controlling effect of the pyridine derivatives (I) on insect pests. The compound numbers correspond to those in Table 2. The compound used for comparison is as follows:

| Compound symbol | Chemical structure | Remarks |
|---|---|---|
| A | [structure: phenyl-O-phenyl-OCH(H)-pyridyl] | Compound disclosed in JP-A-50-18628 (laid open) |

TEST EXAMPLE 1

Metamorphosis inhibitory activity against brown rice planthopper nymphae

An emulfiable concentrate prepared according to Formulation Example 1 was diluted with water to make a predetermined concentration. The dilution was sprayed onto rice plants cultivated in polyethylene cups at a rate of 20 ml/2 pots on a turning table. After air-drying, the plants were infested with about ten 3rd instar nymphae of brown rice planthopper (*Nilaparvata lugens*). After 10 days, the number of normal adults was counted to obtain an emergence inhibitory rate. The results are shown in Table 4.

TABLE 4

| Compound No. | Concentration (ppm) | Inhibitory rate (%) |
|---|---|---|
| 1 | 50 | 100 |
|   | 5 | 100 |
| 2 | 50 | 100 |
| 3 | 50 | 100 |
| 4 | 50 | 100 |
| 5 | 50 | 100 |
|   | 5 | 100 |
|   | 0.5 | 100 |
| 6 | 50 | 100 |
|   | 5 | 100 |
|   | 0.5 | 100 |
|   | 0.05 | 100 |
| 7 | 50 | 100 |
|   | 5 | 100 |
|   | 0.5 | 100 |
| 8 | 50 | 100 |
|   | 5 | 100 |
|   | 0.5 | 100 |
| 9 | 50 | 100 |
|   | 5 | 100 |
|   | 0.5 | 100 |
|   | 0.05 | 100 |
| 10 | 50 | 100 |
|    | 5 | 100 |
| 11 | 50 | 100 |
|    | 5 | 100 |
|    | 0.5 | 100 |
|    | 0.05 | 100 |
| 12 | 50 | 100 |
|    | 5 | 100 |
| 13 | 50 | 100 |
|    | 5 | 100 |
|    | 0.5 | 100 |
| 14 | 50 | 100 |
|    | 5 | 100 |
|    | 0.5 | 100 |
|    | 0.05 | 100 |
| 15 | 50 | 100 |
| 16 | 50 | 100 |
|    | 5 | 100 |
| 17 | 50 | 100 |
|    | 5 | 100 |
|    | 0.5 | 100 |
| 19 | 50 | 100 |
|    | 5 | 100 |
|    | 0.5 | 100 |
|    | 0.05 | 100 |
| 20 | 50 | 100 |
|    | 5 | 100 |
|    | 0.5 | 100 |
|    | 0.05 | 100 |
| 21 | 50 | 100 |
|    | 5 | 100 |
|    | 0.5 | 100 |
|    | 0.05 | 100 |
| 22 | 50 | 100 |
|    | 5 | 100 |
|    | 0.5 | 100 |
|    | 0.05 | 100 |
| 23 | 50 | 100 |
|    | 5 | 100 |
|    | 0.5 | 100 |
|    | 0.05 | 100 |
| 24 | 50 | 100 |
|    | 5 | 100 |
| 25 | 50 | 100 |
| 26 | 50 | 100 |
|    | 5 | 100 |
| 27 | 50 | 100 |
|    | 5 | 100 |

TABLE 4-continued

| Compound No. | Concentration (ppm) | Inhibitory rate (%) |
|---|---|---|
|    | 0.5 | 100 |
|    | 0.05 | 100 |
| 28 | 50 | 100 |
|    | 5 | 100 |
| 29 | 50 | 100 |
|    | 5 | 100 |
| 30 | 50 | 100 |
| 31 | 50 | 100 |
|    | 5 | 100 |
| 32 | 50 | 100 |
|    | 5 | 100 |
| 35 | 50 | 100 |
|    | 5 | 100 |
| 36 | 50 | 100 |
|    | 5 | 100 |
| 37 | 50 | 100 |
| 38 | 50 | 100 |
|    | 5 | 100 |
|    | 0.5 | 100 |
|    | 0.05 | 100 |
| 39 | 50 | 100 |
|    | 5 | 100 |
|    | 0.5 | 100 |
|    | 0.05 | 100 |
| 40 | 50 | 100 |
|    | 5 | 100 |
|    | 0.5 | 100 |
| A  | 50 | 10 |

TEST EXAMPLE 2

Reproduction inhibitory activity against green rice leafhopper

An emulfiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 10 female and male adults of green rice leafhopper (*Nephotettix cincticeps*) were released in each of the cages. After 3 weeks, the number of nymphae was counted to obtain a reproduction inhibitory rate. The results are shown in Table 5.

TABLE 5

| Compound No. | Concentration (ppm) | Inhibitory rate (%) |
|---|---|---|
| 6 | 100 | 100 |
| 11 | 100 | 100 |
| 20 | 100 | 100 |
| 21 | 100 | 100 |
| 22 | 100 | 100 |
| 27 | 100 | 99 |
| A | 100 | 0 |

TEST EXAMPLE 3

Reproduction inhibitory activity against brown rice planthopper

An emulsifiable concentrate prepared according to Formulation Example 1 was diluted with water to make a predetermined concentration. The dilution was sprayed onto rice plants (about 20 cm in height) cultivated in plastic pots (1/5000 are in width) at a rate of 40 ml/2 pots on a turning table. After air-drying, the pots were covered with wire cages, and each 5 female and male adults of brown rice planthopper (*Nilaparvata*

*lugens*) were released in each of the cages. After about 3 weeks, the number of nymphae was counted to obtain a reproduction inhibitory rate. The result are shown in Table 6.

TABLE 6

| Compound No. | Concentration (ppm) | Inhibitory rate (%) |
| --- | --- | --- |
| 6 | 100 | 100 |
| 11 | 100 | 100 |
| 13 | 100 | 100 |
| 20 | 100 | 100 |
| 21 | 100 | 100 |
| 22 | 100 | 100 |
| 27 | 100 | 100 |
| A | 100 | 0 |

TEST EXAMPLE 4

Reproduction inhibitory activity against cotton aphids:

An emulsifier concentrate prepared according to Formulation Example 1 was diluted with water to make a predetermined concentration. The dilution was sprayed onto potted cotton plants (in a stage of 8–9 days after sowing) infested with 1st instar nymphae of cotton aphids (*Aphis gossypii*) at a rate of 30 ml/2 pots on a turning table. Before spraying and one week after spraying, the number of nymphae and adults was counted, and a reproduction inhibitory index was expressed by the following equation:

$$\text{Reproduction inhibitory index} = \frac{\text{Number of individuals one week after spraying per 2 pots}}{\text{Number of individuals before spraying per 2 pots}}$$

wherein the judgement of activity is based on the following standard:
A: less than 1 (excellent effect)
B: from 1 to 3 (slight effect)
C: more than 3 (little effect)
D: same as in the untreated pots (no effect)
The results are shown in Table 7.

TABLE 7

| Compound No. | Concentration (ppm) | Inhibitory rate (%) |
| --- | --- | --- |
| 6 | 10 | A |
| 11 | 10 | A |
| A | 10 | D |

What is claimed is:

1. A pyridine derivative of the formula:

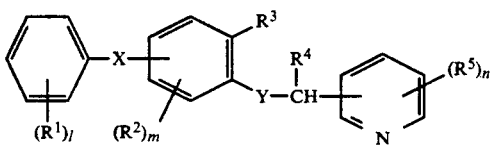

wherein $R^1$ is, the same or different, each a hydrogen atom, a halogen atom, a $C_1$–$C_4$ alkyl group, a $C_1$–$C_4$ haloalkyl group, a $C_1$–$C_3$ alkoxy group, a $C_1$–$C_3$ haloalkoxy group, a cyano group or a nitro group; $R^2$ is, the same or different, each a hydrogen atom, a halogen atom or a methyl group; $R^3$ is a halogen atom or a $C_1$–$C_3$ alkyl group; $R_4$ is a hydrogen atom or a $C_1$–$C_3$ alkyl group; $R^5$ is, the same or different, each a halogen atom, a $C_1$–$C_3$ alkyl group, a $C_1$–$C_3$ haloalkyl group, a $C_1$–$C_3$ alkoxy group or a $C_1$–$C_3$ haloalkoxy group; X is an oxygen atom, a sulfur atom, a carbonyl group, a sulfinyl group, a sulfonyl group, an imino group or a methylene group; Y is an oxygen atom or a sulfur atom; 1 is an integer of 1 to 5; m is an integer of 1 to 3; and n is an integer of 1 to 4.

2. The pyridine derivative according to claim 1, wherein $R^1$ is, the same or different, each a hydrogen atom, a fluorine atom, a chlorine atom, a bromine atom, a methyl group or a trifluoromethyl group.

3. The pyridine derivative according to claim 1, wherein $R^1$ is, the same or different, each a hydrogen atom, a fluorine atom or a chlorine atom, $R^2$ is a hydrogen atom or a chlorine atom, $R^3$ is a fluorine atom, a chlorine atom, a bromine atom or a methyl group, X is an oxygen atom or a methylene group, Y is an oxygen atom, 1 is an integer of 1 or 2, m is an integer of 1 and n is an integer of 1 or 2.

4. The pyridine derivative according to claim 1, wherein $(R^1)_l$ is 2,4-$F_2$, 3,5-$F_2$, 3,4-$Cl_2$, 3-F or 3Cl, $R^2$ is a hydrogen atom, $R^3$ is a chlorine atom, $R^4$ is a hydrogen atom, $R^5$ is a chlorine atom or a methyl group, X is an oxygen atom or a methylene group, Y is an oxygen atom and m and n are each an integer of 1.

5. The pyridine derivative according to claim 1, wherein $R^1$ is a hydrogen atom, $R^2$ is a hydrogen atom, $R^3$ is a chlorine atom, $R^4$ is a hydrogen atom, $R^5$ is a chlorine atom or a methyl group, X is a methylene group, Y is an oxygen atom and m and n are each an integer of 1.

6. The pyridine derivative according to claim 1, wherein $(R^1)_l$ is 2,4-$F_2$, 3,5-$F_2$ or 3-Cl, $R^2$ is a hydrogen atom, $R^3$ is a chlorine atom, $R^4$ is a hydrogen atom, $R^5$ is a chlorine atom or a methyl group, X is an oxygen atom or a methylene group, Y is an oxygen atom and m and n are each an integer of 1.

7. The pyridine derivative according to claim 1, wherein $(R^1)_l$ is 3-F, $R^2$ is a hydrogen atom, $R^3$ is a chlorine atom, $R^4$ is a hydrogen atom, $R^5$ is a chlorine atom or a methyl group, X is a methylene group, Y is an oxygen atom and m and n are each an integer of 1.

8. The pyridine derivative according to claim 1, which is 2-chloro-5-[2-chloro-4-(3,5-difluorophenoxy)-phenoxy]methylpyridine.

9. The pyridine derivative according to claim 1, which is 2-methyl-5-[2-chloro-4-(3,5-difluorophenoxy)-phenoxy]methylpyridine.

10. The pyridine derivative according to claim 1, which is 2-methyl-5-[2-chloro-4-(3,4-dichlorophenoxy)-phenoxy]methylpyridine.

11. The pyridine derivative according to claim 1, which is 2-chloro-5-[2-chloro-4-(3-fluorobenzyl)-phenoxy]methylpyridine.

12. The pyridine derivative according to claim 1, which is 2-chloro-5-[2,5-dichloro-4-(3,5-difluorophenoxy)phenoxy]methylpyridine.

13. The pyridine derivative according to claim 1, which is 2-chloro-5-[2-chloro-5-(3,5-difluorophenoxy)-phenoxy]methylpyridine.

14. The pyridine derivative according to claim 1, which is 2-chloro-5-[2-chloro-4-(3,5-difluorobenzyl)-phenoxy]methylpyridine.

15. The pyridine derivative according to claim 1, which is 2-methyl-5-[2-chloro-4-(2,4-difluorophenoxy)-phenoxy]methylpyridine.

16. The pyridine derivative according to claim 1, which is 2-chloro-5-[2-chloro-4-(3-chlorophenoxy)-phenoxy]methylpyridine.

17. A composition for controlling insect pests which comprises a effective amount of the pyridine derivative according to claim 1 and an inert carrier.

18. A method for controlling insect pests which comprises applying an effective amount of the pyridine derivative according to claim 1 to the insect pests or the locus where the insect pests propagate.

19. A composition for controlling insect pests which comprises an effective amount of the pyridine derivative according to claim 2 and inert carriers.

20. A composition for controlling insect pests which comprises an effective amount of the pyridine derivative according to claim 3 and inert carriers.

21. A composition for controlling insect pests which comprises an effective amount of the pyridine derivative according to claim 4 and inert carriers.

22. A composition for controlling insect pests which comprises an effective amount of the pyridine derivative according to claim 5 and inert carriers.

23. A composition for controlling insect pests which comprises an effective amount of the pyridine derivative according to claim 6 and inert carriers.

24. A composition for controlling insect pests which comprises an effective amount of the pyridine derivative according to claim 7 and inert carries.

* * * * *

UNITED STATES PATENT AND TRADEMARK OFFICE
CERTIFICATE OF CORRECTION

PATENT NO. : 5,151,428
DATED      : Sep. 29, 1992
INVENTOR(S): Sakamoto et al

It is certified that error appears in the above-identified patent and that said Letters Patent is hereby corrected as shown below:

Insert in the first column on the title page the following Assignment Data:

--[73] Assignee:  Sumitomo Chemical Company, Limited, Osaka, Japan--

Signed and Sealed this

Twenty-third Day of November, 1993

Attest:

BRUCE LEHMAN

*Attesting Officer*     Commissioner of Patents and Trademarks